US012569365B2

(12) United States Patent
Meyer et al.

(10) Patent No.: US 12,569,365 B2
(45) Date of Patent: Mar. 10, 2026

(54) FLUID COLLECTION ASSEMBLIES INCLUDING AT LEAST ONE SHAPE MEMORY MATERIAL DISPOSED IN THE CONDUIT

(71) Applicant: PureWick Corporation, El Cajon, CA (US)

(72) Inventors: Andrew Meyer, Oyster Bay, NY (US); Benjamin Jackson, El Cajon, CA (US); Sarah Skelton, Springboro, OH (US); Nicholas Austerman, Atlanta, GA (US); Christopher K. Brooks, Decatur, GA (US); Morgan Rex, El Cajon, CA (US); Cassie Singleton, El Cajon, CA (US); Benjamin Myers, Atlanta, GA (US); Alexis Nunn, Illijay, GA (US)

(73) Assignee: PUREWICK CORPORATION, Covington, GA (US)

( * ) Notice: Subject to any disclaimer, the term of this patent is extended or adjusted under 35 U.S.C. 154(b) by 88 days.

(21) Appl. No.: 17/451,354

(22) Filed: Oct. 19, 2021

(65) Prior Publication Data

US 2022/0117774 A1     Apr. 21, 2022

Related U.S. Application Data

(60) Provisional application No. 63/094,626, filed on Oct. 21, 2020.

(51) Int. Cl.
| | |
|---|---|
| *A61F 5/455* | (2006.01) |
| *A61F 5/44* | (2006.01) |
| *B29C 48/16* | (2019.01) |

(52) U.S. Cl.
CPC ............ *A61F 5/455* (2013.01); *A61F 5/4404* (2013.01); *B29C 48/16* (2019.02)

(58) Field of Classification Search
CPC .......... A61F 5/451; A61F 5/455; A61F 5/453; A61F 5/4553; A61F 5/4556; A61F 5/0096; F16L 11/08
See application file for complete search history.

(56) References Cited

U.S. PATENT DOCUMENTS

| | | |
|---|---|---|
| 737,443 A | 8/1903 | Mooers |
| 1,015,905 A | 1/1912 | Northrop |
| | (Continued) | |

FOREIGN PATENT DOCUMENTS

| | | |
|---|---|---|
| AU | 2018216821 A1 | 8/2019 |
| AU | 2021299304 A1 | 2/2023 |
| | (Continued) | |

OTHER PUBLICATIONS

US 9,908,683 B2, 03/2018, Sandhausen et al. (withdrawn)
(Continued)

*Primary Examiner* — Guy K Townsend
*Assistant Examiner* — Peter Daniel Smith
(74) *Attorney, Agent, or Firm* — Ballard Spahr LLP

(57) ABSTRACT

Embodiments disclosed herein are related to assemblies, systems, and methods of using fluid collection assemblies and systems. The assemblies, systems, and methods of using fluid collection assemblies and systems include at least one shape memory material for forming and maintaining the fluid collection assembly into a selected shape. The shape memory material may enable for selective manipulation of the fluid collection assembly to contour to the anatomical features of variously sized patients.

16 Claims, 9 Drawing Sheets

(56)           References Cited

U.S. PATENT DOCUMENTS

| | | | |
|---|---|---|---|
| 1,032,841 A | 7/1912 | Koenig | |
| 1,178,644 A | 4/1916 | Johnson | |
| 1,387,726 A | 8/1921 | Karge | |
| 1,742,080 A | 12/1929 | Jones | |
| 1,979,899 A | 11/1934 | Obrien et al. | |
| 2,241,010 A | 5/1941 | Chipley | |
| 2,262,772 A | 11/1941 | Peder | |
| 2,326,881 A | 8/1943 | Packer | |
| 2,379,346 A | 6/1945 | Farrell | |
| 2,485,555 A | 10/1949 | Bester | |
| 2,571,357 A | 10/1951 | Charles | |
| 2,613,670 A | 10/1952 | Edward | |
| 2,616,426 A | 11/1952 | Adele | |
| 2,644,234 A | 7/1953 | Earl | |
| 2,648,335 A | 8/1953 | Chambers | |
| 2,859,786 A | 11/1958 | Tupper | |
| 2,944,551 A | 7/1960 | Carl | |
| 2,968,046 A | 1/1961 | Duke | |
| 2,971,512 A | 2/1961 | Reinhardt | |
| 3,032,038 A | 5/1962 | Swinn | |
| 3,077,883 A | 2/1963 | Hill | |
| 3,087,938 A | 4/1963 | Hans et al. | |
| 3,114,916 A | 12/1963 | Hadley | |
| 3,169,528 A * | 2/1965 | Knox, III | A61M 25/09033 |
| | | | 433/91 |
| 3,171,506 A | 3/1965 | Therkel | |
| 3,175,719 A | 3/1965 | Herndon | |
| 3,194,238 A | 7/1965 | Breece | |
| 3,198,994 A | 8/1965 | Hildebrandt et al. | |
| 3,221,742 A | 12/1965 | Egon | |
| 3,312,221 A | 4/1967 | Overment | |
| 3,312,981 A | 4/1967 | Mcguire et al. | |
| 3,349,768 A | 10/1967 | Keane | |
| 3,362,590 A | 1/1968 | Gene | |
| 3,366,116 A | 1/1968 | Huck | |
| 3,398,848 A | 8/1968 | Donovan | |
| 3,400,717 A | 9/1968 | Bruce et al. | |
| 3,406,688 A | 10/1968 | Bruce | |
| 3,424,163 A | 1/1969 | Gravdahl | |
| 3,425,471 A | 2/1969 | Yates | |
| 3,434,565 A | 3/1969 | Fischer | |
| 3,511,241 A | 5/1970 | Lee | |
| 3,512,185 A | 5/1970 | Ellis | |
| 3,520,300 A | 7/1970 | Flower | |
| 3,528,423 A | 9/1970 | Lee | |
| 3,608,552 A | 9/1971 | Broerman | |
| 3,613,123 A | 10/1971 | Langstrom | |
| 3,648,700 A | 3/1972 | Warner | |
| 3,651,810 A | 3/1972 | Ormerod | |
| 3,661,155 A | 5/1972 | Lindan | |
| 3,683,918 A | 8/1972 | Pizzella | |
| 3,699,815 A | 10/1972 | Holbrook | |
| 3,726,277 A | 4/1973 | Hirschman | |
| 3,742,952 A | 7/1973 | Magers et al. | |
| 3,757,355 A | 9/1973 | Allen et al. | |
| 3,788,324 A | 1/1974 | Lim | |
| 3,843,016 A | 10/1974 | Bornhorst et al. | |
| 3,863,638 A | 2/1975 | Rogers et al. | |
| 3,863,798 A | 2/1975 | Kurihara et al. | |
| 3,864,759 A | 2/1975 | Horiuchi | |
| 3,865,109 A | 2/1975 | Elmore et al. | |
| 3,881,486 A | 5/1975 | Fenton | |
| 3,881,489 A | 5/1975 | Hartwell | |
| 3,915,189 A | 10/1975 | Holbrook et al. | |
| 3,931,650 A | 1/1976 | Miller | |
| 3,998,228 A | 12/1976 | Poidomani | |
| 3,999,550 A | 12/1976 | Martin | |
| 4,006,793 A | 2/1977 | Robinson | |
| 4,015,604 A | 4/1977 | Csillag | |
| 4,020,843 A | 5/1977 | Kanall | |
| 4,022,213 A | 5/1977 | Stein | |
| 4,027,776 A | 6/1977 | Douglas | |
| 4,031,897 A | 6/1977 | Graetz | |
| 4,064,962 A | 12/1977 | Hunt | |
| 4,069,817 A | 1/1978 | Fenole et al. | |
| 4,084,589 A | 4/1978 | Kulvi | |
| 4,096,897 A | 6/1978 | Cammarata | |
| 4,116,197 A | 9/1978 | Bermingham | |
| 4,180,178 A | 12/1979 | Turner | |
| 4,187,953 A | 2/1980 | Turner | |
| 4,194,508 A | 3/1980 | Anderson | |
| 4,200,102 A | 4/1980 | Duhamel et al. | |
| 4,202,058 A | 5/1980 | Anderson | |
| 4,203,503 A | 5/1980 | Bertotti et al. | |
| 4,209,076 A | 6/1980 | Bertotti et al. | |
| 4,223,677 A | 9/1980 | Anderson | |
| 4,233,025 A | 11/1980 | Larson et al. | |
| 4,233,978 A | 11/1980 | Hickey | |
| 4,246,901 A | 1/1981 | Frosch et al. | |
| 4,253,542 A | 3/1981 | Ruspa et al. | |
| 4,257,418 A | 3/1981 | Hessner | |
| 4,270,539 A | 6/1981 | Frosch et al. | |
| 4,280,498 A | 7/1981 | Jensen | |
| 4,281,655 A | 8/1981 | Terauchi | |
| 4,292,916 A | 10/1981 | Bradley et al. | |
| 4,330,239 A | 5/1982 | Gannaway | |
| 4,345,341 A | 8/1982 | Saito | |
| 4,349,029 A | 9/1982 | Mott | |
| 4,352,356 A | 10/1982 | Tong | |
| 4,360,933 A | 11/1982 | Kimura et al. | |
| 4,365,363 A | 12/1982 | Windauer | |
| 4,375,841 A | 3/1983 | Vielbig | |
| 4,387,726 A | 6/1983 | Denard | |
| 4,403,991 A | 9/1983 | Hill | |
| 4,421,511 A | 12/1983 | Steer et al. | |
| 4,425,130 A | 1/1984 | Desmarais | |
| 4,446,986 A | 5/1984 | Bowen et al. | |
| 4,453,938 A | 6/1984 | Brendling | |
| 4,457,314 A | 7/1984 | Knowles | |
| 4,476,879 A | 10/1984 | Jackson | |
| 4,526,688 A | 7/1985 | Schmidt et al. | |
| 4,528,703 A | 7/1985 | Kraus | |
| 4,533,354 A | 8/1985 | Jensen et al. | |
| 4,533,357 A | 8/1985 | Hall | |
| D280,438 S | 9/1985 | Wendt | |
| 4,551,141 A | 11/1985 | McNeil | |
| 4,553,968 A | 11/1985 | Komis | |
| 4,568,341 A | 2/1986 | Mitchell et al. | |
| 4,581,026 A | 4/1986 | Schneider | |
| 4,583,983 A | 4/1986 | Einhorn et al. | |
| 4,589,516 A | 5/1986 | Inoue et al. | |
| 4,601,716 A | 7/1986 | Smith | |
| 4,610,675 A | 9/1986 | Triunfol | |
| 4,620,333 A | 11/1986 | Ritter | |
| 4,626,250 A | 12/1986 | Schneider | |
| 4,627,846 A | 12/1986 | Ternstroem | |
| 4,631,061 A | 12/1986 | Martin | |
| 4,650,477 A | 3/1987 | Johnson | |
| 4,655,754 A | 4/1987 | Richmond et al. | |
| 4,656,675 A | 4/1987 | Fajnsztajn | |
| 4,681,570 A | 7/1987 | Dalton | |
| 4,681,572 A | 7/1987 | Tokarz et al. | |
| 4,681,577 A | 7/1987 | Stern et al. | |
| 4,692,160 A | 9/1987 | Nussbaumer | |
| 4,707,864 A | 11/1987 | Ikematsu et al. | |
| 4,713,065 A | 12/1987 | Koot | |
| 4,713,066 A | 12/1987 | Komis | |
| 4,723,953 A | 2/1988 | Pratt et al. | |
| 4,735,841 A | 4/1988 | Sourdet | |
| 4,743,236 A | 5/1988 | Manschot | |
| 4,747,166 A | 5/1988 | Kuntz | |
| 4,752,944 A | 6/1988 | Conrads et al. | |
| 4,769,215 A | 9/1988 | Ehrenkranz | |
| 4,771,484 A | 9/1988 | Mozell | |
| 4,772,280 A | 9/1988 | Rooyakkers | |
| 4,784,654 A | 11/1988 | Beecher | |
| 4,790,830 A | 12/1988 | Hamacher | |
| 4,790,835 A | 12/1988 | Elias | |
| 4,791,686 A | 12/1988 | Taniguchi et al. | |
| 4,795,449 A | 1/1989 | Schneider et al. | |
| 4,798,603 A | 1/1989 | Meyer et al. | |
| 4,799,928 A | 1/1989 | Crowley | |
| 4,804,377 A | 2/1989 | Hanifl et al. | |
| 4,812,053 A | 3/1989 | Bhattacharjee | |

(56) References Cited

U.S. PATENT DOCUMENTS

| | | |
|---|---|---|
| 4,813,943 A | 3/1989 | Smith |
| 4,820,291 A | 4/1989 | Terauchi et al. |
| 4,820,297 A | 4/1989 | Kaufman et al. |
| 4,841,728 A | 6/1989 | Jean et al. |
| 4,846,818 A | 7/1989 | Keldahl et al. |
| 4,846,819 A | 7/1989 | Welch |
| 4,846,824 A | 7/1989 | Schultz et al. |
| 4,846,909 A | 7/1989 | Klug et al. |
| 4,865,595 A | 9/1989 | Heyden |
| 4,880,417 A | 11/1989 | Yabrov et al. |
| 4,882,794 A | 11/1989 | Stewart |
| 4,883,465 A | 11/1989 | Brennan |
| 4,886,498 A | 12/1989 | Newton |
| 4,886,508 A | 12/1989 | Washington |
| 4,886,509 A | 12/1989 | Mattsson |
| 4,889,532 A | 12/1989 | Metz et al. |
| 4,889,533 A | 12/1989 | Beecher |
| 4,890,691 A | 1/1990 | Ching-Ho |
| 4,895,140 A | 1/1990 | Bellak |
| 4,903,254 A | 2/1990 | Haas |
| 4,904,248 A | 2/1990 | Vaillancourt |
| 4,905,692 A | 3/1990 | More |
| 4,911,262 A | 3/1990 | Tani et al. |
| 4,930,997 A | 6/1990 | Bennett |
| 4,936,838 A | 6/1990 | Cross et al. |
| 4,950,262 A | 8/1990 | Takagi |
| 4,955,922 A | 9/1990 | Terauchi |
| 4,957,487 A | 9/1990 | Gerow |
| 4,965,460 A | 10/1990 | Tanaka et al. |
| 4,986,823 A | 1/1991 | Anderson et al. |
| 4,987,849 A | 1/1991 | Sherman |
| 5,002,541 A | 3/1991 | Conkling et al. |
| 5,004,463 A | 4/1991 | Nigay |
| 5,013,308 A | 5/1991 | Sullivan et al. |
| 5,031,248 A | 7/1991 | Kemper |
| 5,045,077 A | 9/1991 | Blake |
| 5,045,283 A | 9/1991 | Patel |
| 5,049,144 A | 9/1991 | Payton |
| 5,053,339 A | 10/1991 | Patel |
| 5,057,092 A * | 10/1991 | Webster, Jr. ........ A61M 25/005 |
| | | 138/123 |
| 5,058,088 A | 10/1991 | Haas et al. |
| 5,071,347 A | 12/1991 | Mcguire |
| 5,078,707 A | 1/1992 | Peter |
| 5,084,037 A | 1/1992 | Barnett |
| 5,100,396 A | 3/1992 | Zamierowski |
| 5,102,404 A | 4/1992 | Goldberg et al. |
| 5,112,324 A | 5/1992 | Wallace |
| 5,137,033 A | 8/1992 | Norton |
| 5,147,301 A | 9/1992 | Ruvio |
| 5,176,667 A | 1/1993 | Debring |
| 5,195,997 A | 3/1993 | Carns |
| 5,196,654 A | 3/1993 | Diflora et al. |
| 5,199,444 A | 4/1993 | Wheeler |
| 5,203,699 A | 4/1993 | Mcguire |
| 5,244,458 A | 9/1993 | Takasu |
| 5,246,454 A | 9/1993 | Peterson |
| 5,267,988 A | 12/1993 | Farkas |
| 5,275,307 A | 1/1994 | Freese |
| 5,282,795 A | 2/1994 | Finney |
| 5,294,983 A | 3/1994 | Ersoz et al. |
| 5,295,979 A | 3/1994 | Delaurentis et al. |
| 5,295,983 A | 3/1994 | Kubo |
| 5,300,052 A | 4/1994 | Kubo |
| 5,304,749 A | 4/1994 | Crandell |
| 5,312,383 A | 5/1994 | Kubalak |
| 5,318,550 A | 6/1994 | Cermak et al. |
| 5,330,457 A | 7/1994 | Cohen |
| 5,330,459 A | 7/1994 | Lavon et al. |
| 5,334,174 A | 8/1994 | Street |
| 5,334,176 A | 8/1994 | Buenger et al. |
| 5,340,840 A | 8/1994 | Park et al. |
| 5,382,244 A | 1/1995 | Telang |
| 5,397,315 A | 3/1995 | Schmidt et al. |
| 5,409,014 A | 4/1995 | Napoli et al. |
| 5,409,475 A | 4/1995 | Steer |
| 5,411,495 A | 5/1995 | Willingham |
| 5,423,784 A | 6/1995 | Metz |
| 5,423,788 A | 6/1995 | Rollins et al. |
| 5,437,836 A | 8/1995 | Yamada |
| 5,456,246 A | 10/1995 | Schmieding et al. |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,582,604 A | 12/1996 | Ahr et al. |
| 5,592,950 A | 1/1997 | Kopelowicz |
| 5,593,389 A | 1/1997 | Chang |
| 5,605,161 A | 2/1997 | Cross |
| 5,614,699 A | 3/1997 | Yashiro et al. |
| 5,618,277 A | 4/1997 | Goulter |
| 5,628,735 A | 5/1997 | Skow |
| 5,632,736 A | 5/1997 | Block |
| 5,636,643 A | 6/1997 | Argenta et al. |
| 5,637,104 A | 6/1997 | Ball et al. |
| 5,662,633 A | 9/1997 | Doak et al. |
| 5,674,212 A | 10/1997 | Osborn et al. |
| 5,678,564 A | 10/1997 | Lawrence et al. |
| 5,678,654 A | 10/1997 | Uzawa |
| 5,681,297 A | 10/1997 | Hashimoto et al. |
| 5,687,429 A | 11/1997 | Rahlff |
| 5,695,485 A | 12/1997 | Duperret et al. |
| 5,700,254 A | 12/1997 | Mcdowall et al. |
| 5,701,612 A | 12/1997 | Daneshvar |
| 5,705,777 A | 1/1998 | Flanigan et al. |
| 5,735,835 A | 4/1998 | Holland |
| 5,752,944 A | 5/1998 | Dann et al. |
| 5,763,333 A | 6/1998 | Suzuki et al. |
| 5,772,644 A | 6/1998 | Bark et al. |
| 5,792,132 A | 8/1998 | Garcia |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,859,393 A | 1/1999 | Cummins et al. |
| 5,865,378 A | 2/1999 | Hollinshead et al. |
| 5,873,869 A | 2/1999 | Hammons et al. |
| 5,876,393 A | 3/1999 | Ahr et al. |
| 5,887,291 A | 3/1999 | Bellizzi |
| 5,891,125 A | 4/1999 | Plumley |
| 5,894,608 A | 4/1999 | Birbara |
| 5,895,349 A | 4/1999 | Tihon |
| D409,303 S | 5/1999 | Oepping |
| 5,911,222 A | 6/1999 | Lawrence et al. |
| 5,956,782 A | 9/1999 | Olguin |
| 5,957,904 A | 9/1999 | Holland |
| 5,968,026 A | 10/1999 | Osborn et al. |
| 5,972,505 A | 10/1999 | Phillips et al. |
| 6,007,526 A | 12/1999 | Passalaqua et al. |
| 6,039,060 A | 3/2000 | Rower |
| 6,050,983 A | 4/2000 | Moore et al. |
| 6,059,762 A | 5/2000 | Boyer et al. |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,220,050 B1 | 4/2001 | Cooksey |
| 6,244,311 B1 | 6/2001 | Hand et al. |
| 6,248,096 B1 | 6/2001 | Dwork et al. |
| 6,263,887 B1 | 7/2001 | Dunn |
| 6,283,246 B1 | 9/2001 | Nishikawa |
| 6,296,627 B1 | 10/2001 | Edwards |
| 6,311,339 B1 | 11/2001 | Kraus |
| 6,316,688 B1 | 11/2001 | Hammons et al. |

(56) References Cited

U.S. PATENT DOCUMENTS

| | | |
|---|---|---|
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,395,956 B1 | 5/2002 | Glasgow et al. |
| 6,398,742 B1 | 6/2002 | Kim |
| 6,406,463 B1 | 6/2002 | Brown |
| 6,409,712 B1 | 6/2002 | Dutari et al. |
| 6,415,888 B2 | 7/2002 | An et al. |
| 6,416,500 B1 | 7/2002 | Wada et al. |
| 6,423,045 B1 | 7/2002 | Wise et al. |
| 6,428,521 B1 | 8/2002 | Droll |
| 6,428,522 B1 | 8/2002 | Dipalma et al. |
| 6,446,454 B1 | 9/2002 | Lee et al. |
| 6,461,340 B1 | 10/2002 | Lenker et al. |
| 6,467,570 B1 | 10/2002 | Herold |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,524,292 B1 | 2/2003 | Dipalma et al. |
| 6,540,729 B1 | 4/2003 | Wada et al. |
| 6,547,771 B2 | 4/2003 | Robertson et al. |
| 6,551,293 B1 | 4/2003 | Mitchell |
| 6,569,133 B2 | 5/2003 | Cheng et al. |
| D476,518 S | 7/2003 | Doppelt |
| 6,592,560 B2 | 7/2003 | Snyder et al. |
| 6,610,038 B1 | 8/2003 | Dipalma et al. |
| 6,618,868 B2 | 9/2003 | Minnick |
| 6,620,142 B1 | 9/2003 | Flueckiger |
| 6,629,651 B1 | 10/2003 | Male et al. |
| 6,635,037 B1 | 10/2003 | Bennett |
| 6,635,038 B2 | 10/2003 | Scovel |
| 6,652,495 B1 | 11/2003 | Walker |
| 6,666,850 B1 | 12/2003 | Ahr et al. |
| 6,685,684 B1 | 2/2004 | Falconer |
| 6,695,828 B1 | 2/2004 | Dipalma et al. |
| 6,699,174 B1 | 3/2004 | Bennett |
| 6,700,034 B1 | 3/2004 | Lindsay et al. |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,122,023 B1 | 10/2006 | Hinoki |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,166,092 B2 | 1/2007 | Elson et al. |
| 7,171,699 B2 | 2/2007 | Ernest et al. |
| 7,171,871 B2 | 2/2007 | Kozak |
| 7,179,951 B2 | 2/2007 | Krishnaswamy-Mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,219,764 B1 | 5/2007 | Forbes |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,549,511 B2 | 6/2009 | Marocco |
| 7,549,512 B2 | 6/2009 | Newberry |
| 7,585,293 B2 | 9/2009 | Vermaak |
| 7,588,560 B1 | 9/2009 | Dunlop |
| 7,637,905 B2 | 12/2009 | Saadat et al. |
| 7,658,730 B2 | 2/2010 | Conley |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns et al. |
| 7,803,144 B1 | 9/2010 | Vollrath |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,016,071 B1 | 9/2011 | Martinus et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,167,860 B1 | 5/2012 | Siegel |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,343,125 B2 | 1/2013 | Kawazoe et al. |
| 8,353,074 B2 | 1/2013 | Krebs |
| 8,353,886 B2 | 1/2013 | Bester et al. |
| D676,241 S | 2/2013 | Merrill |
| 8,388,587 B1 | 3/2013 | Gmuer et al. |
| 8,388,588 B2 | 3/2013 | Wada et al. |
| D679,807 S | 4/2013 | Burgess et al. |
| 8,425,482 B2 | 4/2013 | Khoubnazar |
| 8,434,586 B2 | 5/2013 | Pawelski et al. |
| 8,449,510 B2 | 5/2013 | Martini et al. |

(56) References Cited

U.S. PATENT DOCUMENTS

| | | | |
|---|---|---|---|
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,062 B2 | 10/2013 | Kay |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,586,583 B2 | 11/2013 | Hamblin et al. |
| 8,652,112 B2 | 2/2014 | Johannison et al. |
| 8,669,412 B2 | 3/2014 | Fernkvist et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,145,879 B2 | 9/2015 | Pirovano et al. |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,381,108 B2 | 7/2016 | Longoni et al. |
| 9,382,047 B2 | 7/2016 | Schmidtner et al. |
| 9,402,424 B2 | 8/2016 | Roy |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,709,048 B2 | 7/2017 | Kinjo |
| 9,713,547 B2 | 7/2017 | Lee et al. |
| 9,732,754 B2 | 8/2017 | Huang et al. |
| 9,737,433 B2 | 8/2017 | Joh |
| 9,752,564 B2 | 9/2017 | Arceno et al. |
| 9,788,992 B2 | 10/2017 | Harvie |
| D804,907 S | 12/2017 | Sandoval |
| 9,868,564 B2 | 1/2018 | Mcgirr et al. |
| D814,239 S | 4/2018 | Arora |
| D817,484 S | 5/2018 | Lafond |
| 9,968,908 B2 | 5/2018 | Ladrech et al. |
| 10,010,393 B1 | 7/2018 | Nguyen et al. |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| 10,258,517 B1 | 4/2019 | Maschino et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,500,108 B1 | 12/2019 | Maschino et al. |
| 10,502,198 B2 | 12/2019 | Stumpf et al. |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| RE47,930 E | 4/2020 | Cho |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| 10,806,642 B2 | 10/2020 | Tagomori et al. |
| D901,214 S | 11/2020 | Hu |
| 10,849,799 B2 | 12/2020 | Nishikawa et al. |
| 10,857,025 B2 | 12/2020 | Davis et al. |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,378 B2 | 4/2021 | Ryu et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| 11,002,165 B2 | 5/2021 | Poulin |
| D923,365 S | 6/2021 | Wang |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,090,183 B2 | 8/2021 | Sanchez et al. |
| 11,160,695 B2 | 11/2021 | Febo et al. |
| 11,160,697 B2 | 11/2021 | Maschino et al. |
| 11,168,420 B2 | 11/2021 | Kinugasa et al. |
| 11,179,506 B2 | 11/2021 | Barr et al. |
| 11,199,116 B2 | 12/2021 | Ostromecki et al. |
| 11,207,206 B2 | 12/2021 | Sharma et al. |
| 11,226,376 B2 | 1/2022 | Yamauchi et al. |
| 11,253,389 B2 | 2/2022 | Sharma et al. |
| 11,253,407 B2 | 2/2022 | Miao et al. |
| 11,326,586 B2 | 5/2022 | Milner et al. |
| 11,369,508 B2 | 6/2022 | Ecklund et al. |
| 11,369,524 B2 | 6/2022 | Hubbard et al. |
| 11,376,152 B2 | 7/2022 | Sanchez et al. |
| 11,382,786 B2 | 7/2022 | Sanchez et al. |
| 11,382,788 B2 | 7/2022 | Hjorth et al. |
| 11,389,318 B2 | 7/2022 | Radl et al. |
| 11,395,871 B2 | 7/2022 | Radl et al. |
| 11,399,990 B2 | 8/2022 | Suyama |
| 11,426,303 B2 | 8/2022 | Davis et al. |
| 11,504,265 B2 | 11/2022 | Godinez et al. |
| 11,529,252 B2 | 12/2022 | Glithero et al. |
| 11,547,788 B2 | 1/2023 | Radl et al. |
| 11,806,266 B2 | 11/2023 | Sanchez et al. |
| 11,839,567 B2 | 12/2023 | Davis et al. |
| D1,010,109 S | 1/2024 | Ecklund et al. |
| 11,857,716 B2 | 1/2024 | Lee et al. |

(56) References Cited

U.S. PATENT DOCUMENTS

| | | |
|---|---|---|
| 11,865,030 B2 | 1/2024 | Davis et al. |
| 11,890,221 B2 | 2/2024 | Ulreich et al. |
| 11,911,160 B2 | 2/2024 | Woodard et al. |
| 11,925,575 B2 | 3/2024 | Newton |
| 11,938,053 B2 | 3/2024 | Austermann et al. |
| 11,944,740 B2 | 4/2024 | Hughett et al. |
| 11,994,122 B2 | 5/2024 | Bodain |
| 11,998,475 B2 | 6/2024 | Becker et al. |
| 12,023,457 B2 | 7/2024 | Mann et al. |
| 12,042,422 B2 | 7/2024 | Davis et al. |
| D1,038,385 S | 8/2024 | Ecklund et al. |
| 12,064,372 B2 | 8/2024 | Godinez et al. |
| 12,070,432 B2 | 8/2024 | Tourchak et al. |
| 12,090,083 B2 | 9/2024 | Ecklund et al. |
| 12,133,813 B2 | 11/2024 | Ulreich et al. |
| 12,138,195 B2 | 11/2024 | Alder et al. |
| 12,186,229 B2 | 1/2025 | Davis et al. |
| 12,245,966 B2 | 3/2025 | Newton |
| 2001/0037097 A1 | 11/2001 | Cheng et al. |
| 2001/0037098 A1 | 11/2001 | Snyder |
| 2001/0054426 A1 | 12/2001 | Knudson et al. |
| 2002/0019614 A1 | 2/2002 | Woon |
| 2002/0026161 A1 | 2/2002 | Grundke |
| 2002/0026163 A1 | 2/2002 | Grundke |
| 2002/0042945 A1 | 4/2002 | Sands |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2002/0193762 A1 | 12/2002 | Suydam |
| 2003/0004436 A1 | 1/2003 | Schmidt et al. |
| 2003/0032931 A1 | 2/2003 | Grundke et al. |
| 2003/0032944 A1 | 2/2003 | Cawood |
| 2003/0073964 A1 | 4/2003 | Palumbo et al. |
| 2003/0074724 A1 | 4/2003 | Sands |
| 2003/0120178 A1 | 6/2003 | Heki |
| 2003/0129178 A1 | 7/2003 | Wegman et al. |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0147863 A1 | 7/2004 | Diaz et al. |
| 2004/0147894 A1 | 7/2004 | Mizutani et al. |
| 2004/0147895 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0181201 A1 | 9/2004 | Mizutani et al. |
| 2004/0191919 A1 | 9/2004 | Unger et al. |
| 2004/0194792 A1 | 10/2004 | Zhuang et al. |
| 2004/0200936 A1 | 10/2004 | Opperthauser |
| 2004/0207530 A1 | 10/2004 | Nielsen |
| 2004/0236292 A1 | 11/2004 | Tazoe et al. |
| 2004/0243075 A1 | 12/2004 | Harvie |
| 2004/0254547 A1 | 12/2004 | Okabe et al. |
| 2005/0010182 A1 | 1/2005 | Parks et al. |
| 2005/0010197 A1 | 1/2005 | Lau et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0131361 A1 | 6/2005 | Miskie |
| 2005/0137557 A1 | 6/2005 | Swiecicki et al. |
| 2005/0137560 A1 | 6/2005 | Mizutani et al. |
| 2005/0137561 A1 | 6/2005 | Mizutani et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0197645 A1 | 9/2005 | Karpowicz et al. |
| 2005/0215969 A1 | 9/2005 | Mizutani et al. |
| 2005/0273069 A1 | 12/2005 | Mizutani et al. |
| 2005/0273920 A1 | 12/2005 | Marinas |
| 2005/0277903 A1 | 12/2005 | Mizutani et al. |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0113334 A1 | 6/2006 | Mikhail et al. |
| 2006/0155214 A1 | 7/2006 | Wightman |
| 2006/0171997 A1 | 8/2006 | Gruenbacher et al. |
| 2006/0180566 A1 | 8/2006 | Mataya |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1* | 6/2007 | Rushlander ............ F16L 11/112 |
| | | 138/121 |
| 2007/0149935 A1 | 6/2007 | Dirico |
| 2007/0191804 A1 | 8/2007 | Coley |
| 2007/0203464 A1 | 8/2007 | Green et al. |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0077099 A1 | 3/2008 | House |
| 2008/0091153 A1 | 4/2008 | Harvie |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0226541 A1 | 9/2009 | Scholz et al. |
| 2009/0234312 A1 | 9/2009 | Otoole et al. |
| 2009/0251510 A1 | 10/2009 | Noro et al. |

(56) References Cited

U.S. PATENT DOCUMENTS

| | | |
|---|---|---|
| 2009/0259206 A1 | 10/2009 | Kai et al. |
| 2009/0264840 A1 | 10/2009 | Virginio |
| 2009/0270822 A1 | 10/2009 | Medeiros |
| 2009/0281510 A1 | 11/2009 | Fisher |
| 2009/0283982 A1 | 11/2009 | Thomas |
| 2009/0306610 A1 | 12/2009 | Van Den Heuvel et al. |
| 2010/0004612 A1 | 1/2010 | Thevenin |
| 2010/0031429 A1 | 2/2010 | Kim et al. |
| 2010/0032789 A1 | 2/2010 | Schoen et al. |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0179493 A1 | 7/2010 | Heagle et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0137273 A1 | 6/2011 | Muellejans et al. |
| 2011/0145993 A1 | 6/2011 | Rader et al. |
| 2011/0152802 A1 | 6/2011 | DiCamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0198904 A1 | 8/2011 | Thomas et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1* | 5/2012 | Wheaton ................. A61F 5/453 |
| | | 128/885 |
| 2012/0116336 A1 | 5/2012 | Sharma et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0209216 A1* | 8/2012 | Jensen ................. A61M 35/003 |
| | | 604/239 |
| 2012/0209225 A1 | 8/2012 | Hu et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0019374 A1 | 1/2013 | Schwartz |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0110059 A1 | 5/2013 | Kossow et al. |
| 2013/0138064 A1 | 5/2013 | Stroebech et al. |
| 2013/0150813 A1 | 6/2013 | Gordon et al. |
| 2013/0165880 A1 | 6/2013 | Amos et al. |
| 2013/0218112 A1 | 8/2013 | Thompson |
| 2013/0245496 A1 | 9/2013 | Wells et al. |
| 2013/0245586 A1 | 9/2013 | Jha |
| 2013/0274711 A1 | 10/2013 | O'day |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0039440 A1 | 2/2014 | Doescher |
| 2014/0058347 A1 | 2/2014 | Marquette |
| 2014/0107599 A1 | 4/2014 | Fink et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0276501 A1 | 9/2014 | Cisko |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209188 A1 | 7/2015 | Scheremet et al. |
| 2015/0209194 A1 | 7/2015 | Heyman |
| 2015/0267862 A1 | 9/2015 | Mishler |
| 2015/0290421 A1 | 10/2015 | Glickman et al. |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0359996 A1 | 12/2015 | Arora et al. |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0051395 A1 | 2/2016 | Ugarte M.D. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0136338 A1 | 5/2016 | Lee et al. |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0367726 A1 | 12/2016 | Gratzer |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0042724 A1 | 2/2017 | Ugarte |
| 2017/0042748 A1 | 2/2017 | Griffin |
| 2017/0100276 A1 | 4/2017 | Joh |
| 2017/0107312 A1 | 4/2017 | Hinayama et al. |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0238911 A1 | 8/2017 | Duval |

(56) References Cited

U.S. PATENT DOCUMENTS

| | | |
|---|---|---|
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1* | 9/2017 | Sanchez ............... A61F 5/4404 |
| 2017/0266658 A1 | 9/2017 | Bruno et al. |
| 2017/0281399 A1 | 10/2017 | Vanmiddendorp et al. |
| 2017/0281419 A1 | 10/2017 | Pintado |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0348139 A1 | 12/2017 | Newton et al. |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1* | 8/2018 | Davis ..................... A61B 5/208 |
| 2018/0256384 A1 | 9/2018 | Kasirye |
| 2018/0271694 A1 | 9/2018 | Fernandez et al. |
| 2018/0317892 A1 | 11/2018 | Catlin |
| 2018/0325748 A1 | 11/2018 | Sharma et al. |
| 2019/0001030 A1 | 1/2019 | Braga et al. |
| 2019/0021899 A1 | 1/2019 | Met |
| 2019/0038451 A1 | 2/2019 | Harvie |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |
| 2019/0133126 A1 | 5/2019 | Modak et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0226189 A1 | 7/2019 | Braxton |
| 2019/0240079 A1 | 8/2019 | Tuli |
| 2019/0247222 A1 | 8/2019 | Ecklund et al. |
| 2019/0247223 A1 | 8/2019 | Brun et al. |
| 2019/0247623 A1 | 8/2019 | Helm et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365303 A1 | 12/2019 | Bullington et al. |
| 2019/0365307 A1 | 12/2019 | Laing et al. |
| 2019/0365561 A1 | 12/2019 | Newton et al. |
| 2019/0374373 A1 | 12/2019 | Joh |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-Schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0179177 A1 | 6/2020 | Erdem et al. |
| 2020/0187918 A1 | 6/2020 | Wiygul |
| 2020/0206015 A1 | 7/2020 | Langer |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0375810 A1 | 12/2020 | Carlin et al. |
| 2020/0384242 A1 | 12/2020 | Havard et al. |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0023279 A1 | 1/2021 | Radl et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1* | 3/2021 | Blabas ................... A61F 5/451 |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0211568 A1 | 7/2021 | Zhou et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0315726 A1 | 10/2021 | Lin |
| 2021/0315727 A1 | 10/2021 | Jiang |
| 2021/0353449 A1 | 11/2021 | Sharma et al. |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0031290 A1 | 2/2022 | Weed |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |

(56) References Cited

U.S. PATENT DOCUMENTS

| | | |
|---|---|---|
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0118165 A1 | 4/2022 | Knapp et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1 | 9/2022 | Johannes et al. |
| 2022/0280357 A1 | 9/2022 | Jagannathan et al. |
| 2022/0280710 A1 | 9/2022 | Agrawal et al. |
| 2022/0287689 A1 | 9/2022 | Johannes |
| 2022/0287867 A1 | 9/2022 | Jones et al. |
| 2022/0287868 A1 | 9/2022 | Garvey et al. |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1 | 10/2022 | Kriscovich et al. |
| 2022/0331170 A1 | 10/2022 | Erdem et al. |
| 2022/0339023 A1 | 10/2022 | Davis et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0387693 A1 | 12/2022 | Bannwart et al. |
| 2022/0395390 A1 | 12/2022 | Brooks |
| 2022/0395391 A1 | 12/2022 | Saunders et al. |
| 2022/0401252 A1 | 12/2022 | Warren |
| 2022/0409419 A1 | 12/2022 | Garvey et al. |
| 2022/0409422 A1 | 12/2022 | Schneider et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0049924 A1 | 2/2023 | Johannes et al. |
| 2023/0052238 A1 | 2/2023 | Oluwasogo |
| 2023/0062944 A1 | 3/2023 | Vollenberg et al. |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1 | 3/2023 | Hughett et al. |
| 2023/0091118 A1 | 3/2023 | Watson |
| 2023/0099821 A1 | 3/2023 | Radl et al. |
| 2023/0099991 A1 | 3/2023 | Bianchi et al. |
| 2023/0105001 A1 | 4/2023 | Whittome et al. |
| 2023/0110577 A1 | 4/2023 | Choi |
| 2023/0138269 A1 | 5/2023 | Abdelal et al. |
| 2023/0145365 A1 | 5/2023 | Martin et al. |
| 2023/0155253 A1 | 5/2023 | Yin et al. |
| 2023/0190511 A1 | 6/2023 | Sharma et al. |
| 2023/0210504 A1 | 7/2023 | Kuroda et al. |
| 2023/0210685 A1 | 7/2023 | Fallows et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1 | 8/2023 | Mann et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277360 A1 | 9/2023 | Lambert et al. |
| 2023/0277362 A1 | 9/2023 | Davis et al. |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |
| 2024/0033148 A1 | 2/2024 | Gordon et al. |
| 2024/0041638 A1 | 2/2024 | Johannes et al. |
| 2024/0058160 A1 | 2/2024 | Young Joyner et al. |
| 2024/0058161 A1 | 2/2024 | Ulreich et al. |
| 2024/0058520 A1 | 2/2024 | Mn et al. |
| 2024/0065881 A1 | 2/2024 | Kuroda et al. |
| 2024/0082044 A1 | 3/2024 | Nguyen et al. |
| 2024/0099874 A1 | 3/2024 | Sanchez et al. |
| 2024/0108268 A1 | 4/2024 | Woodard et al. |
| 2024/0110318 A1 | 4/2024 | Bendt et al. |
| 2024/0122773 A1 | 4/2024 | Nguyen et al. |
| 2024/0123134 A1 | 4/2024 | Kharkar et al. |
| 2024/0148539 A1 | 5/2024 | Austermann et al. |
| 2024/0156633 A1 | 5/2024 | Fallows et al. |
| 2024/0252343 A1 | 8/2024 | Voda |
| 2024/0261131 A1 | 8/2024 | Garvey et al. |
| 2024/0268986 A1 | 8/2024 | Barnes et al. |
| 2024/0268989 A1 | 8/2024 | Martin et al. |
| 2024/0269027 A1 | 8/2024 | Tourchak et al. |
| 2024/0285425 A1 | 8/2024 | Donohoe et al. |
| 2024/0325190 A1 | 10/2024 | Minchew et al. |
| 2024/0358539 A1 | 10/2024 | Gallup |
| 2024/0358542 A1 | 10/2024 | Richardson et al. |
| 2024/0374414 A1 | 11/2024 | Richardson et al. |
| 2025/0009552 A1 | 1/2025 | Blabas et al. |
| 2025/0073055 A1 | 3/2025 | Ecklund et al. |
| 2025/0107920 A1 | 4/2025 | Fallows et al. |
| 2025/0107921 A1 | 4/2025 | Sanchez et al. |

FOREIGN PATENT DOCUMENTS

| | | |
|---|---|---|
| AU | 2022349367 A1 | 4/2024 |
| CA | 2165286 C | 9/1999 |
| CA | 2354132 A1 | 6/2000 |
| CA | 2359091 C | 9/2003 |
| CA | 2488867 C | 8/2007 |
| CA | 202184840 U | 4/2012 |
| CA | 107847384 A | 3/2018 |
| CA | 3050918 A1 | 8/2018 |
| CA | 3098571 A1 | 11/2019 |
| CA | 3188651 A1 | 7/2023 |
| CN | 2269203 Y | 12/1997 |
| CN | 1332620 A | 1/2002 |
| CN | 1434693 A | 8/2003 |
| CN | 1533755 A | 10/2004 |
| CN | 1602825 A | 4/2005 |
| CN | 1720888 A | 1/2006 |
| CN | 2936204 Y | 8/2007 |
| CN | 101262836 A | 9/2008 |
| CN | 101522148 A | 9/2009 |
| CN | 102159159 A | 8/2011 |
| CN | 102481441 A | 5/2012 |
| CN | 202463712 U | 10/2012 |
| CN | 202950810 U | 5/2013 |
| CN | 103533968 A | 1/2014 |
| CN | 103717180 A | 4/2014 |
| CN | 204562697 U | 8/2015 |
| CN | 105411783 A | 3/2016 |
| CN | 105451693 A | 3/2016 |
| CN | 105534632 A | 5/2016 |
| CN | 106132360 A | 11/2016 |
| CN | 205849719 U | 1/2017 |
| CN | 205924282 U | 2/2017 |
| CN | 106726089 A | 5/2017 |
| CN | 107920912 A | 4/2018 |
| CN | 108420590 A | 8/2018 |

(56) References Cited

FOREIGN PATENT DOCUMENTS

| | | | |
|---|---|---|---|
| CN | 209285902 | U | 8/2019 |
| CN | 110381883 | A | 10/2019 |
| CN | 211198839 | U | 8/2020 |
| CN | 111991136 | A | 11/2020 |
| CN | 112022488 | A | 12/2020 |
| CN | 212234893 | U | 12/2020 |
| CN | 212466312 | U | 2/2021 |
| CN | 112566550 | A | 3/2021 |
| CN | 112603184 | A | 4/2021 |
| CN | 213490035 | U | 6/2021 |
| CN | 114007493 | A | 2/2022 |
| CN | 114375187 | A | 4/2022 |
| CN | 116096332 | A | 5/2023 |
| DE | 79818 | C | 10/1893 |
| DE | 1516466 | A1 | 6/1969 |
| DE | 2721330 | A1 | 11/1977 |
| DE | 2742298 | A1 | 3/1978 |
| DE | 9407554.9 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 102005037762 | B3 | 9/2006 |
| DE | 102011103783 | A1 | 12/2012 |
| DE | 102012112818 | A1 | 6/2014 |
| DE | 202015104597 | U1 | 7/2016 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0220962 | A1 | 5/1987 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0483730 | A1 | 5/1992 |
| EP | 0610638 | A1 | 8/1994 |
| EP | 0613355 | A1 | 9/1994 |
| EP | 0613355 | B1 | 1/1997 |
| EP | 0680296 | B1 | 5/1997 |
| EP | 0787472 | A1 | 8/1997 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3569205 | B1 | 6/2023 |
| EP | 4382082 | A2 | 6/2024 |
| EP | 4445881 | A2 | 10/2024 |
| EP | 4464288 | A2 | 11/2024 |
| EP | 4527361 | A2 | 3/2025 |
| FR | 2826704 | A1 | 1/2003 |
| GB | 871820 | A | 7/1961 |
| GB | 873045 | A | 7/1961 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2260907 | A | 5/1993 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| GE | 2199750 | A | 7/1988 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58188016 | U | 12/1983 |
| JP | S59118161 | A | 7/1984 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H05123349 | A | 5/1993 |
| JP | H05123350 | A | 5/1993 |
| JP | H0626264 | U | 4/1994 |
| JP | 3087938 | B2 | 10/1995 |
| JP | H085630 | A | 1/1996 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000152953 | A | 6/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003528691 | A | 9/2003 |
| JP | 2004057578 | A | 2/2004 |
| JP | 2004130056 | A | 4/2004 |
| JP | 2004267400 | A | 9/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |

(56) References Cited

FOREIGN PATENT DOCUMENTS

| | | | |
|---|---|---|---|
| JP | 2007259898 A | 10/2007 |
| JP | 4039641 B2 | 11/2007 |
| JP | 2008005975 A | 1/2008 |
| JP | 2009509570 A | 3/2009 |
| JP | 2009165887 A | 7/2009 |
| JP | 2009525776 A | 7/2009 |
| JP | 2010504150 A | 2/2010 |
| JP | 2010058795 A | 3/2010 |
| JP | 2010081981 A | 4/2010 |
| JP | 2010166954 A | 8/2010 |
| JP | 4640772 B2 | 12/2010 |
| JP | 2010536439 A | 12/2010 |
| JP | 2011500225 A | 1/2011 |
| JP | 2011030962 A | 2/2011 |
| JP | 4747166 B2 | 5/2011 |
| JP | 2011087823 A | 5/2011 |
| JP | 4801218 B1 | 8/2011 |
| JP | 2011202664 A | 10/2011 |
| JP | 2011218130 A | 11/2011 |
| JP | 2011224070 A | 11/2011 |
| JP | 3175719 U | 4/2012 |
| JP | 2012523869 A | 10/2012 |
| JP | 2013238608 A | 11/2013 |
| JP | 2014521960 A | 8/2014 |
| JP | 2015092945 A | 5/2015 |
| JP | 2015513678 A | 5/2015 |
| JP | 3198994 B2 | 7/2015 |
| JP | 2015221390 A | 12/2015 |
| JP | 2016521191 A | 7/2016 |
| JP | 2017014698 A | 1/2017 |
| JP | 2017070400 A | 4/2017 |
| JP | 2017512603 A | 5/2017 |
| JP | 2017201272 A | 11/2017 |
| JP | 2019010375 A | 1/2019 |
| JP | 2019076342 A | 5/2019 |
| JP | 2019525811 A | 9/2019 |
| JP | 2019170942 A | 10/2019 |
| JP | 2019533492 A | 11/2019 |
| JP | 2020520775 A | 7/2020 |
| JP | 2020124425 A | 8/2020 |
| JP | 2021007472 A | 1/2021 |
| JP | 2021041145 A | 3/2021 |
| JP | 2021120686 A | 8/2021 |
| JP | 2021522009 A | 8/2021 |
| JP | 2021522013 A | 8/2021 |
| JP | 2021522019 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20080005516 A | 1/2008 |
| KR | 20090072069 A | 7/2009 |
| KR | 20090104426 A | 10/2009 |
| KR | 20090110359 A | 10/2009 |
| KR | 20120005922 A | 1/2012 |
| KR | 20140039485 A | 4/2014 |
| KR | 101432639 B1 | 8/2014 |
| KR | 20180106659 A | 10/2018 |
| KR | 20180108774 A | 10/2018 |
| KR | 20230034343 A | 3/2023 |
| PT | 2068717 E | 6/2013 |
| SE | 505542 C2 | 9/1997 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9303690 A1 | 3/1993 |
| WO | 9307839 A1 | 4/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0079497 A1 | 12/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2004026195 A1 | 4/2004 |
| WO | 2005051252 A1 | 6/2005 |
| WO | 2005060558 A2 | 7/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007134608 A2 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012020506 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |

(56) References Cited

FOREIGN PATENT DOCUMENTS

| | | | |
|---|---|---|---|
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017001846 | A1 | 1/2017 |
| WO | 2017075226 | A1 | 5/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018235026 | A1 | 12/2018 |
| WO | 2018235065 | A1 | 12/2018 |
| WO | 2019004404 | A1 | 1/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020033752 | A1 | 2/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016056 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022029662 | A1 | 2/2022 |
| WO | 2022031943 | A1 | 2/2022 |
| WO | 2022035745 | A1 | 2/2022 |
| WO | 2022051220 | A1 | 3/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150290 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022173803 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2022251184 | A1 | 12/2022 |
| WO | 2022251425 | A1 | 12/2022 |
| WO | 2022271783 | A1 | 12/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |

(56)                  References Cited

FOREIGN PATENT DOCUMENTS

| WO | 2023018656 A1 | 2/2023 |
| WO | 2023018657 A1 | 2/2023 |
| WO | 2023023777 A1 | 3/2023 |
| WO | 2023034139 A1 | 3/2023 |
| WO | 2023034453 A1 | 3/2023 |
| WO | 2023038945 A1 | 3/2023 |
| WO | 2023038950 A1 | 3/2023 |
| WO | 2023049109 A1 | 3/2023 |
| WO | 2023049156 A1 | 3/2023 |
| WO | 2023049175 A1 | 3/2023 |
| WO | 2023086394 A1 | 5/2023 |
| WO | 2023149884 A1 | 8/2023 |
| WO | 2023149902 A1 | 8/2023 |
| WO | 2023149903 A1 | 8/2023 |
| WO | 2023154390 A1 | 8/2023 |
| WO | 2023163725 A1 | 8/2023 |
| WO | 2023191764 A1 | 10/2023 |
| WO | 2023244238 A1 | 12/2023 |
| WO | 2024043871 A1 | 2/2024 |
| WO | 2024058788 A1 | 3/2024 |
| WO | 2024253655 A1 | 12/2024 |
| WO | 2025034959 A1 | 2/2025 |
| WO | 2025038087 A1 | 2/2025 |
| WO | 2025038088 A1 | 2/2025 |
| WO | 2025071622 A1 | 4/2025 |

OTHER PUBLICATIONS

Advisory Action for U.S. Appl. No. 16/905,400 mailed Feb. 16, 2022.

Corrected Notice of Allowability for U.S. Appl. No. 17/330,657 mailed Dec. 9, 2021.

Final Office Action for U.S. Appl. No. 16/452,145 mailed Mar. 25, 2022.

Final Office Action for U.S. Appl. No. 16/904,868 mailed Mar. 10, 2022.

Final Office Action for U.S. Appl. No. 16/905,400 mailed Dec. 9, 2021.

International Search Report and Written Opinion from International Application No. PCT/US2020/057562 mailed Jan. 27, 2021.

International Search Report and Written Opinion from International Application No. PCT/US2021/026607 mailed Jul. 29, 2021.

International Search Report and Written Opinion from International Application No. PCT/US2021/043893 mailed Nov. 22, 2021.

International Search Report and Written Opinion from International Application No. PCT/US2021/044699 mailed Nov. 22, 2021.

International Search Report and Written Opinion from International Application No. PCT/US2021/045188 mailed Jan. 26, 2022.

International Search Report and Written Opinion from International Application No. PCT/US2021/047536 mailed Dec. 23, 2021.

International Search Report and Written Opinion from International Application No. PCT/US2021/048211 mailed Dec. 22, 2021.

International Search Report and Written Opinion from International Application No. PCT/US2021/048661 mailed Feb. 14, 2022.

International Search Report and Written Opinion from International Application No. PCT/US2021/049404 mailed Jan. 18, 2022.

International Search Report and Written Opinion from International Application No. PCT/US2021/051456 mailed Jan. 19, 2022.

International Search Report and Written Opinion from International Application No. PCT/US2021/053593 mailed Apr. 11, 2022.

International Search Report and Written Opinion from International Application No. PCT/US2021/056566 mailed Feb. 11, 2022.

International Search Report and Written Opinion from International Application No. PCT/US2021/060993 mailed Mar. 18, 2022.

International Search Report and Written Opinion from International Application No. PCT/US2021/062440 mailed Mar. 28, 2022.

International Search Report and Written Opinion from International Application No. PCT/US2022/011108 mailed Apr. 22, 2022.

International Search Report and Written Opinion from International Application No. PCT/US2022/011281 mailed Apr. 25, 2022.

International Search Report and Written Opinion from International Application No. PCT/US2022/012794 mailed May 3, 2022.

International Search Report and Written Opinion from International Application No. PCT/US2022015471 mailed May 16, 2022.

Non-Final Office Action for U.S. Appl. No. 16/245,726 mailed Jan. 21, 2022.

Non-Final Office Action for U.S. Appl. No. 16/369,676 mailed Mar. 31, 2022.

Non-Final Office Action for U.S. Appl. No. 16/433,773 mailed Apr. 21, 2022.

Non-Final Office Action for U.S. Appl. No. 16/449,039 mailed Dec. 8, 2021.

Non-Final Office Action for U.S. Appl. No. 16/478,180 mailed Oct. 22, 2021.

Non-Final Office Action for U.S. Appl. No. 16/905,400 mailed Apr. 27, 2022.

Non-Final Office Action for U.S. Appl. No. 29/741,751 mailed Jan. 18, 2022.

Notice of Allowance for U.S. Appl. No. 16/899,956 mailed Apr. 19, 2022.

Notice of Allowance for U.S. Appl. No. 16/899,956 mailed Dec. 29, 2021.

Notice of Allowance for U.S. Appl. No. 17/088,272 mailed Mar. 4, 2022.

Notice of Allowance for U.S. Appl. No. 17/088,272 mailed Nov. 24, 2021.

Notice of Allowance for U.S. Appl. No. 17/330,657 mailed Mar. 16, 2022.

Notice of Allowance for U.S. Appl. No. 17/330,657 mailed Nov. 26, 2021.

Restriction Requirement for U.S. Appl. No. 16/433,773 mailed Dec. 7, 2021.

U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/384,196, filed Dec. 19, 2016.
U.S. Appl. No. 16/245,726, filed Jan. 11, 2019.
U.S. Appl. No. 17/394,055, filed Aug. 4, 2021.
U.S. Appl. No. 17/450,864, filed Oct. 14, 2021.
U.S. Appl. No. 17/451,345, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/485,578, filed Apr. 14, 2017.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/967,977, filed Jan. 30, 2020.
U.S. Appl. No. 63/008,112, filed Apr. 10, 2020.
U.S. Appl. No. 63/094,646, filed Oct. 21, 2020.

(56)               References Cited

OTHER PUBLICATIONS

U.S. Appl. No. 63/109,084, filed Nov. 3, 2020.
U.S. Appl. No. 63/133,892, filed Jan. 5, 2021.
U.S. Appl. No. 63/138,878, filed Jan. 19, 2021.
U.S. Appl. No. 63/191,558, filed May 21, 2021.
U.S. Appl. No. 63/192,289, filed May 24, 2021.
U.S. Appl. No. 63/208,262, filed Jun. 8, 2021.
U.S. Appl. No. 63/230,897, filed Aug. 9, 2021.
U.S. Appl. No. 63/299,208, filed Jan. 13, 2022.
"Rising Warrior Insulated Gallon Jug Cover", https://www.amazon.com/Rising-Warrior-Insulated-Sleeve, 2021, 2 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000, 2020, 2 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hwang , et al., "Multifunctional Smart Skin Adhesive Patches for Advanced Health Care", Adv. Healthcare Mater, 2018, pp. 1-20.
Jagota , et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee , et al., "Continuous Fabrication of Wide-Tip Microstructures for Bio-Inspired Dry Adhesives via Tip Inking Process", Journal of Chemistry, Jan. 2, 2019, pp. 1-5.
Parness , et al., "A microfabricated wedge-shaped adhesive array displaying gecko-like dynamic adhesion, directionality", J.R. Soc. Interface, 2009, pp. 1223-1232.
Tsipenyuk , et al., "Use of biomimetic hexagonal surface texture in friction against lubricated skin", Journal of The Royal Society—Interface, 2014, pp. 1-6.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Feb. 15, 2023.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/904,868 mailed Jun. 15, 2022.
Advisory Action for U.S. Appl. No. 17/662,700 mailed Jan. 30, 2023.
Final Office Action for U.S. Appl. No. 16/245,726 mailed Nov. 25, 2022.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/478,180 mailed May 31, 2023.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/444,792 mailed Jun. 15, 2023.
Final Office Action for U.S. Appl. No. 17/451,345 mailed May 3, 2023.
Final Office Action for U.S. Appl. No. 17/662,700 mailed Sep. 30, 2022.
International Search Report and Written Opinion from International Application No. PCT/IB2021/057173 mailed Nov. 5, 2021.
International Search Report and Written Opinion from International Application No. PCT/US2021/039866 mailed Oct. 7, 2021.
International Search Report and Written Opinion from International Application No. PCT/US2021/055515 mailed Jan. 28, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.

(56) References Cited

OTHER PUBLICATIONS

International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Non-Final Office Action for U.S. Appl. No. 16/433,773 mailed Apr. 11, 2023.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,258 mailed Apr. 26, 2023.
Non-Final Office Action for U.S. Appl. No. 16/478,180 mailed Dec. 20, 2022.
Non-Final Office Action for U.S. Appl. No. 16/904,868 mailed Mar. 15, 2023.
Non-Final Office Action for U.S. Appl. No. 17/051,550 mailed Dec. 15, 2022.
Non-Final Office Action for U.S. Appl. No. 17/051,585 mailed Mar. 29, 2023.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/444,792 mailed Feb. 10, 2023.
Non-Final Office Action for U.S. Appl. No. 17/446,256 mailed Apr. 13, 2023.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/453,260 mailed Mar. 14, 2023.
Non-Final Office Action for U.S. Appl. No. 17/501,591 mailed Apr. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/655,464 mailed Mar. 14, 2023.
Non-Final Office Action for U.S. Appl. No. 17/661,090 mailed Jul. 6, 2023.
Non-Final Office Action for U.S. Appl. No. 17/662,700 mailed Jul. 22, 2022.
Non-Final Office Action for U.S. Appl. No. 17/663,330 mailed Jun. 29, 2023.
Non-Final Office Action for U.S. Appl. No. 17/664,487 mailed Jun. 8, 2023.
Notice of Allowance for U.S. Appl. No. 16/245,726 mailed Jul. 6, 2023.
Notice of Allowance for U.S. Appl. No. 16/449,039 mailed Dec. 15, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/905,400 mailed Aug. 17, 2022.
Notice of Allowance for U.S. Appl. No. 17/051,554 mailed Jul. 6, 2023.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/461,036 mailed Oct. 6, 2022.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/663,046 mailed Jan. 30, 2023.
Notice of Allowance for U.S. Appl. No. 18/299,788 mailed Jul. 24, 2023.
Notice of Allowance for U.S. Appl. No. 29/741,751 mailed Jun. 9, 2022.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Text Messages to Lorena Eckert Re Prototype PureWick Holder dated Apr. 16, 2022.
U.S. Appl. No. 15/611,587, filed Jun. 1, 2017.
U.S. Appl. No. 17/664,487, filed May 23, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.

(56)　　　　　References Cited

OTHER PUBLICATIONS

U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 62/967,158, filed Jan. 26, 2020.
U.S. Appl. No. 62/991,754, filed Mar. 19, 2020.
U.S. Appl. No. 63/241,328, filed Sep. 7, 2021.
U.S. Appl. No. 63/308,190, filed Feb. 9, 2022.
*PureWick Corporation* v. *Sage Products, LLC* Transcripts vol. 5, Apr. 1, 2022, 72 pages.
*PureWick Corporation* v. *Sage Products, LLC* Transcripts vol. 1, Mar. 28, 2022, 99 pages.
*PureWick Corporation* v. *Sage Products, LLC* Transcripts vol. 2, Mar. 29, 2022, 106 pages.
*PureWick Corporation* v. *Sage Products, LLC* Transcripts vol. 3, Mar. 30, 2022, 115 pages.
*PureWick Corporation* v. *Sage Products, LLC* Transcripts vol. 4, Mar. 31, 2022, 117 pages.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Pieper , et al., "An external urine-collection device for women: A clinical trial", Journal of ER Nursing, vol. 20, No. 2, Mar./Apr. 1993, pp. 51-55.
VINAS , "A Solution for an Awkward—But Serious—Subject", http://www.aero-news.net/index.cfm?do=main.textpost&id=69ae2bb1-838b-4098-a7b5-7flbb2505688 last accessed Feb. 8, 2021, 3 pages.

Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl.No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/899,956 mailed Apr. 19, 2021.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.

(56) References Cited

OTHER PUBLICATIONS

International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 29/624,661 mailed Aug. 4, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.

(56) References Cited

OTHER PUBLICATIONS

Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 17/088,272 mailed Aug. 5, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.
Restriction Requirement for U.S. Appl. No. 16/478,180 mailed May 25, 2021.
U.S. Appl. No. 14/433,773, filed Apr. 3, 2020.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/612,325, filed Jun. 2, 2017.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/461,036 mailed Aug. 30, 2021.
U.S. Appl. No. 17/494,578, filed Oct. 5, 2021.
U.S. Appl. No. 29/741,751, filed Jul. 15, 2020.
U.S. Appl. No. 62/452,437, filed Jan. 31, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.

U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.

(56) References Cited

OTHER PUBLICATIONS

U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
Defendant and Counterclaim Plaintiff Sage Products, LLC's Answer, Defenses, and Counterclaims to Plaintiff's Amended Complaint, Nov. 1, 2019.
Memorandum Order, Feb. 2021, 14 pgs.
Sage's Initial Invalidity Contentions Regarding U.S. Pat. Nos. 8,287,508; 10,226,375; and 10,390,989, May 29, 2020,193 pages.
Exhibit A to PureWick's Fourth Supplemental Response to Interrogatory No. 3, Mar. 2021, 21 pages.
PureWick's Supplemental Response to Interrogatory No. 6 Exhibit C: U.S. Pat. No. 6,287,508, Sep. 2020, 21 pages.
Exhibit B to PureWick's Supplemental Response to Interrogatory No. 6: U.S. Pat. No. 8,287,508, 25 pages.
Exhibit B to PureWick's Supplemental Response to Interrogatory No. 6: U.S. Pat. No. 10,390,989, 26 pages.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Sage's Second Supplemental Invalidity Contentions Regarding U.S. Pat. Nos. 8,287,508, 10,226,375, 10,390,989, and 10,376,407, 292 pages.
Boehringer CareDry System—Second Generation for Non-Invasive Urinary Management for Females, Mar. 2021, 3 pgs.
Exhibit B to PureWick's Supplemental Response to Interrogatory No. 6: U.S. Pat. No. 10,226,376, 38 pages.
Excerpts from the 508 (U.S. Pat. No. 8,278,508) Patent's Prosecution History, 2020, 99 pages.
Sage's Second Notice of Deposition of PureWick Corporation, C.A. No. 19-1508-MN, Feb. 2021, 10 pages.
Sage's First Notice of Deposition of PureWick Corporation, C.A. No. 19-1508-MN, Feb. 2021, 14 pages.
Sage's Supplemental Statement Regarding References and Combinations, C.A. No. 19-1508-MN, 3 pages.
Sixth Supplemental Responses to Sage Products' First Set of Interrogatories (No. 1-11) to PureWick Corporation, C.A. No. 19-1508-MN, Apr. 2021, 39 pages.
Seventh Supplemental Responses to Sage Products' First Set of Interrogatories (No. 1-11) to PureWick Corporation, C.A. No. 19-1508-MN, Apr. 2021, 41 pages.
Plaintiff's Opening Claim Construction Brief, Case No. 19-1508-MN, Oct. 16, 2020, 26 pages.
Plaintiff's Identification of Claim Terms and Proposed Constructions, Case No. 19-1508-MN, 3 pages.
PureWick's Response to Interrogatory No. 9 in PureWick, LLC v. Sage Products, LLC, Case No. 19-1508-MN, Mar. 23, 2020, 6 pages.
Sage's Preliminary Identification of Claim Elements and Proposed Constructions for U.S. Patent Nos. 8,287,508, 10,226,376, 10,390,989 and 10,376,407, Case No. 19-1508-MN, 7 pages.
Decision Granting Institution of Inter Partes Review for patent No. 8,287,508, Case No. 2020-01426, Feb. 17, 2021, 39 pages.
Corrected Certificate of Service, Case No. IPR2020-01426, Patent No. 8,287,508, 2020, 2 pages.
Declaration of Diane K. Newman Curriculum Vitae, Petition for Interparties Review, 2020, pp. 1-199.

"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, Omni Medical, 8 pages.
"AMXDmax In-Flight Bladder Relief", Omni Medical; Omni Medical Systems, Inc., 2015.
"AMXDX—Advanced Mission Extender Device Brochure", Omni Medical, Omni Brochure—http://www.omnimedicalsys.com/uploads/AMXDFixedWing.pdf, 2 pages.
"External Urine Management for Female Anatomy", https://www.stryker.com/US/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via% 3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, Omni Presentation https://www.omnimedicalsys.com/uploads/AMXDmax_HSD.pdf, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology 2005-06", British Department of Health, Nov. 2006, 40 pages.
"Step by Step How Ur24 WorksHome", http://medicalpatentur24.com, last accessed Dec. 6, 2017, Aug. 30, 2017, 4 pages.
"Underwear that absorbs your period", Thinx!, https://www.shethinx.com/pages/thinx-it-works last accessed Jun. 24, 2020, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Hollister, Female Urinary and Pouch and Male Urinary Pouch Brochure, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
Hollister, "Retracted Penis Pouch by Hollister", Vitality Medical.com, https://www.vitalitymedical.com/hollister-retracted-penis-pouch.html last accessed Jun. 24, 2020, 6 pages.
Jennewein, "Connect Graduates 7 Startups in Tech, Life Sciences", https://timesofsandiego.com/business/2015/08/16/connect-graduates-7-startups-in-tech-life-sciences/, Aug. 2015, 2 pages.
Macaulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
Purewick, "Incontinence Relief for Women", Presentation, Sep. 23, 2015, 7 pages.
Pytlik, "Super Absorbent Polymers", University of Buffalo, http://www.courses.sens.buffalo.edu/ce435/Diapers/Diapers.html, accessed on Feb. 17, 2017.

(56)            References Cited

OTHER PUBLICATIONS

Sachtman, "New Relief for Pilots? It Depends", Wired, https://www.wired.com/2008/05/pilot-relief/, 2008, 2 pages.

Advisory Action for U.S. Appl. No. 16/433,773 mailed Dec. 29, 2023.

Advisory Action for U.S. Appl. No. 16/449,039 mailed Jan. 25, 2024.

Advisory Action for U.S. Appl. No. 16/478,180 mailed Sep. 7, 2023.

Advisory Action for U.S. Appl. No. 16/904,868 mailed Jan. 2, 2024.

Advisory Action for U.S. Appl. No. 17/051,550 mailed Sep. 8, 2023.

Advisory Action for U.S. Appl. No. 17/051,585 mailed Oct. 17, 2023.

Advisory Action for U.S. Appl. No. 17/179,116 mailed Jan. 8, 2024.

Advisory Action for U.S. Appl. No. 17/444,792 mailed Aug. 25, 2023.

Advisory Action for U.S. Appl. No. 17/446,256 mailed Dec. 8, 2023.

Advisory Action for U.S. Appl. No. 17/448,811 mailed Nov. 15, 2023.

Advisory Action for U.S. Appl. No. 17/451,345 mailed Oct. 20, 2023.

Advisory Action for U.S. Appl. No. 17/453,260 mailed Dec. 22, 2023.

Advisory Action for U.S. Appl. No. 17/501,591 mailed Feb. 22, 2024.

Advisory Action for U.S. Appl. No. 17/653,137 mailed Dec. 1, 2023.

Advisory Action for U.S. Appl. No. 17/655,464 mailed Dec. 13, 2023.

Advisory Action for U.S. Appl. No. 18/164,800 mailed Feb. 12, 2024.

Communication of Notice of Opposition of European Application No. 17807547.9 mailed Jan. 5, 2024.

Corrected Notice of Allowability for U.S. Appl. No. 16/369,676 mailed Dec. 7, 2023.

Corrected Notice of Allowability for U.S. Appl. No. 17/326,980 mailed Feb. 8, 2024.

Final Office Action for U.S. Appl. No. 16/369,676 mailed Aug. 31, 2023.

Final Office Action for U.S. Appl. No. 16/433,773 mailed Oct. 10, 2023.

Final Office Action for U.S. Appl. No. 16/449,039 mailed Nov. 21, 2023.

Final Office Action for U.S. Appl. No. 16/452,258 mailed Dec. 21, 2023.

Final Office Action for U.S. Appl. No. 16/904,868 mailed Nov. 2, 2023.

Final Office Action for U.S. Appl. No. 17/051,399 mailed Jan. 8, 2024.

Final Office Action for U.S. Appl. No. 17/179,116 mailed Oct. 31, 2023.

Final Office Action for U.S. Appl. No. 17/446,256 mailed Sep. 19, 2023.

Final Office Action for U.S. Appl. No. 17/446,654 mailed Jan. 31, 2024.

Final Office Action for U.S. Appl. No. 17/448,811 mailed Aug. 3, 2023.

Final Office Action for U.S. Appl. No. 17/450,864 mailed Dec. 28, 2023.

Final Office Action for U.S. Appl. No. 17/453,260 mailed Oct. 5, 2023.

Final Office Action for U.S. Appl. No. 17/501,591 mailed Nov. 14, 2023.

Final Office Action for U.S. Appl. No. 17/646,771 mailed Dec. 21, 2023.

Final Office Action for U.S. Appl. No. 17/653,137 mailed Sep. 21, 2023.

Final Office Action for U.S. Appl. No. 17/655,464 mailed Sep. 1, 2023.

Final Office Action for U.S. Appl. No. 17/661,090 mailed Dec. 11, 2023.

Final Office Action for U.S. Appl. No. 17/663,330 mailed Dec. 12, 2023.

Final Office Action for U.S. Appl. No. 17/664,487 mailed Jan. 4, 2024.

Final Office Action for U.S. Appl. No. 18/139,523 mailed Dec. 22, 2023.

Final Office Action for U.S. Appl. No. 18/140,751 mailed Jan. 17, 2024.

Final Office Action for U.S. Appl. No. 18/164,800 mailed Dec. 6, 2023.

International Search Report and Written Opinion from International Application No. PCT/US2022/050909 mailed Jul. 24, 2023.

International Search Report and Written Opinion from International Application No. PCT/US2023/012696 mailed Jul. 6, 2023.

International Search Report and Written Opinion from International Application No. PCT/US2023/018474 mailed Sep. 11, 2023.

International Search Report and Written Opinion from International Application No. PCT/US2023/024805 mailed Dec. 14, 2023.

Issue Notification for U.S. Appl. No. 16/245,726 mailed Oct. 18, 2023.

Issue Notification for U.S. Appl. No. 17/461,036 mailed Oct. 11, 2023.

Issue Notification for U.S. Appl. No. 17/663,046 mailed Dec. 20, 2023.

Issue Notification for U.S. Appl. No. 18/299,788 mailed Feb. 21, 2024.

Non-Final Office Action for U.S. Appl. No. 16/452,145 mailed Nov. 2, 2023.

Non-Final Office Action for U.S. Appl. No. 16/478,180 mailed Nov. 7, 2023.

Non-Final Office Action for U.S. Appl. No. 17/051,399 mailed Aug. 18, 2023.

Non-Final Office Action for U.S. Appl. No. 17/051,550 mailed Oct. 24, 2023.

Non-Final Office Action for U.S. Appl. No. 17/051,585 mailed Jan. 8, 2024.

Non-Final Office Action for U.S. Appl. No. 17/051,600 mailed Jan. 17, 2024.

Non-Final Office Action for U.S. Appl. No. 17/444,792 mailed Nov. 17, 2023.

Non-Final Office Action for U.S. Appl. No. 17/446,256 mailed Feb. 13, 2024.

Non-Final Office Action for U.S. Appl. No. 17/446,654 mailed Sep. 8, 2023.

Non-Final Office Action for U.S. Appl. No. 17/447,123 mailed Jan. 24, 2024.

Non-Final Office Action for U.S. Appl. No. 17/448,811 mailed Jan. 17, 2024.

Non-Final Office Action for U.S. Appl. No. 17/451,345 mailed Jan. 17, 2024.

Non-Final Office Action for U.S. Appl. No. 17/453,560 mailed Oct. 16, 2023.

Non-Final Office Action for U.S. Appl. No. 17/645,821 mailed Oct. 25, 2023.

Non-Final Office Action for U.S. Appl. No. 17/653,137 mailed Jan. 18, 2024.

Non-Final Office Action for U.S. Appl. No. 17/657,474 mailed Sep. 12, 2023.

Non-Final Office Action for U.S. Appl. No. 17/664,914 mailed Jan. 31, 2024.

Non-Final Office Action for U.S. Appl. No. 17/808,354 mailed Nov. 28, 2023.

Non-Final Office Action for U.S. Appl. No. 18/134,857 mailed Jan. 25, 2024.

Non-Final Office Action for U.S. Appl. No. 18/139,523 mailed Aug. 17, 2023.

Non-Final Office Action for U.S. Appl. No. 18/140,163 mailed Nov. 9, 2023.

Non-Final Office Action for U.S. Appl. No. 18/140,751 mailed Sep. 14, 2023.

(56) References Cited

OTHER PUBLICATIONS

Non-Final Office Action for U.S. Appl. No. 18/198,464 mailed Dec. 7, 2023.
Notice of Allowance for U.S. Appl. No. 16/369,676 mailed Nov. 14, 2023.
Notice of Allowance for U.S. Appl. No. 17/051,550 mailed Feb. 7, 2024.
Notice of Allowance for U.S. Appl. No. 17/051,554 mailed Oct. 18, 2023.
Notice of Allowance for U.S. Appl. No. 17/326,980 mailed Jan. 29, 2024.
Notice of Allowance for U.S. Appl. No. 17/453,560 mailed Jan. 31, 2024.
Notice of Allowance for U.S. Appl. No. 17/662,700 mailed Nov. 15, 2023.
Notice of Allowance for U.S. Appl. No. 18/299,788 mailed Nov. 6, 2023.
Restriction Requirement for U.S. Appl. No. 17/051,600 mailed Sep. 21, 2023.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/451,719, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/681,987, filed Feb. 7, 2024.
U.S. Appl. No. 18/682,006, filed Feb. 7, 2024.
U.S. Appl. No. 63/150,640, filed Feb. 18, 2021.
U.S. Appl. No. 63/596,012, filed Nov. 3, 2023.
U.S. Appl. No. 63/608,553, filed Dec. 11, 2023.
Merriam-Webster Dictionary, "Embed Definition & Meaning", https://www.merriam-webster.com/dictionary/embed last accessed Aug. 3, 2023, 2003.
Wikipedia Article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/446,654 mailed Apr. 15, 2024.
Advisory Action for U.S. Appl. No. 17/450,864 mailed Mar. 21, 2024.
Advisory Action for U.S. Appl. No. 17/451,345 mailed Jul. 3, 2024.
Advisory Action for U.S. Appl. No. 17/645,821 mailed Jul. 2, 2024.
Advisory Action for U.S. Appl. No. 17/646,771 mailed Feb. 29, 2024.
Advisory Action for U.S. Appl. No. 17/661,090 mailed Feb. 26, 2024.

Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Final Office Action for U.S. Appl. No. 16/478,180 mailed Feb. 28, 2024.
Final Office Action for U.S. Appl. No. 17/051,600 mailed Jun. 27, 2024.
Final Office Action for U.S. Appl. No. 17/444,792 mailed Apr. 3, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/645,821 mailed Apr. 3, 2024.
Final Office Action for U.S. Appl. No. 17/808,354 mailed Apr. 10, 2024.
Final Office Action for U.S. Appl. No. 18/140,163 mailed Mar. 27, 2024.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/077208 mailed May 10, 2024.
Issue Notification for U.S. Appl. No. 16/449,039 mailed Jun. 19, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/657,474 mailed Jun. 19, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/452,258 mailed Jun. 20, 2024.
Non-Final Office Action for U.S. Appl. No. 16/904,868 mailed Mar. 12, 2024.
Non-Final Office Action for U.S. Appl. No. 17/179,116 mailed Feb. 26, 2024.
Non-Final Office Action for U.S. Appl. No. 17/446,654 mailed Jun. 25, 2024.
Non-Final Office Action for U.S. Appl. No. 17/450,864 mailed May 29, 2024.
Non-Final Office Action for U.S. Appl. No. 17/595,747 mailed Jun. 7, 2024.
Non-Final Office Action for U.S. Appl. No. 17/597,673 mailed Mar. 20, 2024.
Non-Final Office Action for U.S. Appl. No. 17/646,771 mailed Apr. 24, 2024.

(56) References Cited

OTHER PUBLICATIONS

Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 18/003,029 mailed Mar. 26, 2024.
Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/389,009 mailed May 24, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 17/326,980 mailed Apr. 5, 2024.
Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 18/198,464 mailed Apr. 17, 2024.
Restriction Requirement for U.S. Appl. No. 17/527,769 mailed Jun. 17, 2024.
Restriction Requirement for U.S. Appl. No. 17/667,097 mailed Mar. 20, 2024.
U.S. Appl. No. 17/444,792, filed Aug. 10, 2021.
U.S. Appl. No. 18/249,577, filed Oct. 19, 2021.
U.S. Appl. No. 18/610,523, filed Mar. 20, 2024.
U.S. Appl. No. 18/662,216, filed May 13, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/757,964, filed Jun. 28, 2024.
U.S. Appl. No. 18/758,025, filed Jun. 28, 2024.
U.S. Appl. No. 63/561,893, filed Dec. 11, 2023.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Wikipedia Article, "Decibel", https://web.archive.org/web/2020041521917/https://en.wikipedia.org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Advisory Action for U.S. Appl. No. 17/051,585 mailed Oct. 8, 2024.

Advisory Action for U.S. Appl. No. 17/444,792 mailed Jul. 8, 2024.
Advisory Action for U.S. Appl. No. 17/446,256 mailed Nov. 19, 2024.
Advisory Action for U.S. Appl. No. 17/597,673 mailed Jan. 7, 2025.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 18/003,029 mailed Jan. 8, 2025.
Advisory Action for U.S. Appl. No. 18/134,857 mailed Oct. 23, 2024.
Advisory Action for U.S. Appl. No. 18/164,800 mailed Jan. 8, 2025.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/646,771 mailed Jan. 17, 2025.
Corrected Notice of Allowability for U.S. Appl. No. 17/664,914 mailed Aug. 9, 2024.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 16/452,258 mailed Jan. 6, 2025.
Final Office Action for U.S. Appl. No. 17/051,585 mailed Jul. 5, 2024.
Final Office Action for U.S. Appl. No. 17/446,256 mailed Aug. 7, 2024.
Final Office Action for U.S. Appl. No. 17/446,654 mailed Dec. 18, 2024.
Final Office Action for U.S. Appl. No. 17/451,345 mailed Feb. 6, 2025.
Final Office Action for U.S. Appl. No. 17/595,747 mailed Dec. 12, 2024.
Final Office Action for U.S. Appl. No. 17/597,673 mailed Oct. 22, 2024.
Final Office Action for U.S. Appl. No. 17/625,941 mailed Feb. 18, 2025.
Final Office Action for U.S. Appl. No. 17/653,137 mailed Aug. 7, 2024.
Final Office Action for U.S. Appl. No. 17/653,314 mailed Jan. 30, 2025.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/164,800 mailed Oct. 22, 2024.
International Search Report and Written Opinion from International Application No. PCT/US2023/031432 mailed Feb. 29, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
International Search Report and Written Opinion from International Application No. PCT/US2024/053681 mailed Jan. 27, 2025.

(56)         References Cited

OTHER PUBLICATIONS

Issue Notification for U.S. Appl. No. 16/369,676 mailed Oct. 2, 2024.

Issue Notification for U.S. Appl. No. 16/452,145 mailed Oct. 23, 2024.

Issue Notification for U.S. Appl. No. 17/179,116 mailed Dec. 25, 2024.

Issue Notification for U.S. Appl. No. 17/326,980 mailed Jul. 10, 2024.

Issue Notification for U.S. Appl. No. 17/447,123 mailed Nov. 13, 2024.

Issue Notification for U.S. Appl. No. 17/448,811 mailed Jul. 3, 2024.

Issue Notification for U.S. Appl. No. 17/450,864 mailed Jan. 8, 2025.

Issue Notification for U.S. Appl. No. 17/453,260 mailed Jul. 10, 2024.

Issue Notification for U.S. Appl. No. 17/453,560 mailed Aug. 7, 2024.

Issue Notification for U.S. Appl. No. 17/529,769 mailed Feb. 19, 2025.

Issue Notification for U.S. Appl. No. 17/661,090 mailed Feb. 5, 2025.

Issue Notification for U.S. Appl. No. 17/662,700 mailed Oct. 23, 2024.

Issue Notification for U.S. Appl. No. 17/664,914 mailed Nov. 6, 2024.

Issue Notification for U.S. Appl. No. 17/667,097 mailed Dec. 11, 2024.

Issue Notification for U.S. Appl. No. 18/140,163 mailed Dec. 4, 2024.

Issue Notification for U.S. Appl. No. 18/140,751 mailed Feb. 12, 2025.

Issue Notification for U.S. Appl. No. 18/198,464 mailed Nov. 20, 2024.

Issue Notification for U.S. Appl. No. 18/389,009 mailed Dec. 18, 2024.

Issue Notification for U.S. Appl. No. 18/426,795 mailed Feb. 19, 2025.

Non-Final Office Action for U.S. Appl. No. 16/478,180 mailed Aug. 7, 2024.

Non-Final Office Action for U.S. Appl. No. 17/378,015 mailed Jul. 5, 2024.

Non-Final Office Action for U.S. Appl. No. 17/444,792 mailed Oct. 30, 2024.

Non-Final Office Action for U.S. Appl. No. 17/446,256 mailed Dec. 13, 2024.

Non-Final Office Action for U.S. Appl. No. 17/451,345 mailed Jul. 25, 2024.

Non-Final Office Action for U.S. Appl. No. 17/597,408 mailed Aug. 15, 2024.

Non-Final Office Action for U.S. Appl. No. 17/614,173 mailed Sep. 24, 2024.

Non-Final Office Action for U.S. Appl. No. 17/625,941 mailed Nov. 4, 2024.

Non-Final Office Action for U.S. Appl. No. 17/628,411 mailed Sep. 23, 2024.

Non-Final Office Action for U.S. Appl. No. 17/645,821 mailed Sep. 6, 2024.

Non-Final Office Action for U.S. Appl. No. 17/653,137 mailed Jan. 28, 2025.

Non-Final Office Action for U.S. Appl. No. 17/653,314 mailed Aug. 29, 2024.

Non-Final Office Action for U.S. Appl. No. 17/653,920 mailed Nov. 27, 2024.

Non-Final Office Action for U.S. Appl. No. 17/749,340 mailed Aug. 14, 2024.

Non-Final Office Action for U.S. Appl. No. 17/757,311 mailed Oct. 22, 2024.

Non-Final Office Action for U.S. Appl. No. 17/758,316 mailed Aug. 28, 2024.

Non-Final Office Action for U.S. Appl. No. 17/759,697 mailed Dec. 4, 2024.

Non-Final Office Action for U.S. Appl. No. 17/808,354 mailed Dec. 13, 2024.

Non-Final Office Action for U.S. Appl. No. 17/907,125 mailed Dec. 13, 2024.

Non-Final Office Action for U.S. Appl. No. 18/139,523 mailed Aug. 26, 2024.

Non-Final Office Action for U.S. Appl. No. 18/426,795 mailed Aug. 9, 2024.

Non-Final Office Action for U.S. Appl. No. 18/451,080 mailed Jul. 30, 2024.

Non-Final Office Action for U.S. Appl. No. 18/584,002 mailed Sep. 19, 2024.

Notice of Allowance for U.S. Appl. No. 16/452,145 mailed Jul. 11, 2024.

Notice of Allowance for U.S. Appl. No. 16/478,180 mailed Dec. 16, 2024.

Notice of Allowance for U.S. Appl. No. 16/904,868 mailed Jan. 21, 2025.

Notice of Allowance for U.S. Appl. No. 16/904,868 mailed Sep. 29, 2024.

Notice of Allowance for U.S. Appl. No. 17/051,585 mailed Dec. 26, 2024.

Notice of Allowance for U.S. Appl. No. 17/179,116 mailed Sep. 13, 2024.

Notice of Allowance for U.S. Appl. No. 17/447,123 mailed Jul. 26, 2024.

Notice of Allowance for U.S. Appl. No. 17/450,864 mailed Sep. 18, 2024.

Notice of Allowance for U.S. Appl. No. 17/501,591 mailed Jul. 31, 2024.

Notice of Allowance for U.S. Appl. No. 17/501,591 mailed Nov. 20, 2024.

Notice of Allowance for U.S. Appl. No. 17/527,769 mailed Nov. 20, 2024.

Notice of Allowance for U.S. Appl. No. 17/596,629 mailed Jan. 29, 2025.

Notice of Allowance for U.S. Appl. No. 17/646,771 mailed Dec. 17, 2024.

Notice of Allowance for U.S. Appl. No. 17/661,090 mailed Oct. 30, 2024.

Notice of Allowance for U.S. Appl. No. 17/663,330 mailed Nov. 20, 2024.

Notice of Allowance for U.S. Appl. No. 17/664,914 mailed Jul. 26, 2024.

Notice of Allowance for U.S. Appl. No. 17/667,097 mailed Aug. 28, 2024.

Notice of Allowance for U.S. Appl. No. 17/749,340 mailed Feb. 14, 2025.

Notice of Allowance for U.S. Appl. No. 18/134,857 mailed Feb. 20, 2025.

Notice of Allowance for U.S. Appl. No. 18/140,163 mailed Aug. 21, 2024.

Notice of Allowance for U.S. Appl. No. 18/140,751 mailed Nov. 1, 2024.

Notice of Allowance for U.S. Appl. No. 18/198,464 mailed Jul. 30, 2024.

Notice of Allowance for U.S. Appl. No. 18/389,009 mailed Aug. 28, 2024.

Notice of Allowance for U.S. Appl. No. 18/415,080 mailed Dec. 30, 2024.

Notice of Allowance for U.S. Appl. No. 18/426,795 mailed Nov. 20, 2024.

Notice of Allowance for U.S. Appl. No. 18/584,002 mailed Jan. 8, 2025.

Restriction Requirement for U.S. Appl. No. 17/596,629 mailed Sep. 19, 2024.

Restriction Requirement for U.S. Appl. No. 17/625,941 mailed Aug. 7, 2024.

(56) References Cited

OTHER PUBLICATIONS

Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
U.S. Appl. No. 17/013,822, filed Sep. 7, 2020.
U.S. Appl. No. 18/728,604, filed Jul. 12, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/103,165, filed Feb. 11, 2025.
U.S. Appl. No. 63/181,709, filed Apr. 29, 2021.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, Abut Definition and Meaning", Dictionary.com, https://www.dictionary.com/browse/abut, 2024, 1 page.
Advisory Action for U.S. Appl. No. 16/452,258 mailed May 5, 2025.
Advisory Action for U.S. Appl. No. 17/446,654 mailed Feb. 28, 2025.
Advisory Action for U.S. Appl. No. 17/451,345 mailed May 13, 2025.
Advisory Action for U.S. Appl. No. 17/595,747 mailed Mar. 17, 2025.
Advisory Action for U.S. Appl. No. 17/653,314 mailed Apr. 8, 2025.
Advisory Action for U.S. Appl. No. 17/655,464 mailed Feb. 25, 2025.
Advisory Action for U.S. Appl. No. 17/664,487 mailed Apr. 24, 2025.
Advisory Action for U.S. Appl. No. 17/757,311 mailed Jul. 2, 2025.
Corrected Notice of Allowability for U.S. Appl. No. 17/996,253 mailed Apr. 28, 2025.
Corrected Notice of Allowability for U.S. Appl. No. 18/134,857 mailed Mar. 14, 2025.
Corrected Notice of Allowance for U.S. Appl. No. 17/444,792 mailed Jun. 24, 2025.
Final Office Action for U.S. Appl. No. 17/378,015 mailed Jun. 18, 2025.
Final Office Action for U.S. Appl. No. 17/446,256 mailed Jun. 11, 2025.
Final Office Action for U.S. Appl. No. 17/597,408 mailed Mar. 24, 2025.
Final Office Action for U.S. Appl. No. 17/614,173 mailed May 20, 2025.
Final Office Action for U.S. Appl. No. 17/628,411 mailed Apr. 30, 2025.
Final Office Action for U.S. Appl. No. 17/653,137 mailed Jun. 25, 2025.
Final Office Action for U.S. Appl. No. 17/653,920 mailed Apr. 24, 2025.
Final Office Action for U.S. Appl. No. 17/757,311 mailed Mar. 31, 2025.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/907,125 mailed Apr. 30, 2025.
Final Office Action for U.S. Appl. No. 18/139,523 mailed May 8, 2025.
International Search Report and Written Opinion from International Application No. PCT/US2023/036875 mailed May 31, 2024.
International Search Report and Written Opinion from International Application No. PCT/US2023/077205 mailed Jul. 19, 2024.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
International Search Report and Written Opinion from International Application No. PCT/US2025/018913 mailed Jun. 18, 2025.
Issue Notification for U.S. Appl. No. 16/478,180 mailed Mar. 5, 2025.
Issue Notification for U.S. Appl. No. 16/904,868 mailed Apr. 30, 2025.
Issue Notification for U.S. Appl. No. 17/051,585 mailed Mar. 26, 2025.
Issue Notification for U.S. Appl. No. 17/444,792 mailed Jun. 25, 2025.
Issue Notification for U.S. Appl. No. 17/501,591 mailed Mar. 5, 2025.
Issue Notification for U.S. Appl. No. 17/597,673 mailed Jun. 4, 2025.
Issue Notification for U.S. Appl. No. 17/646,771 mailed Mar. 19, 2025.
Issue Notification for U.S. Appl. No. 17/663,330 mailed Feb. 26, 2025.
Issue Notification for U.S. Appl. No. 17/749,340 mailed May 28, 2025.
Issue Notification for U.S. Appl. No. 17/758,316 mailed Jun. 25, 2025.
Issue Notification for U.S. Appl. No. 18/134,857 mailed May 28, 2025.
Issue Notification for U.S. Appl. No. 18/415,080 mailed Apr. 9, 2025.
Issue Notification for U.S. Appl. No. 18/584,002 mailed Apr. 16, 2025.
Non-Final Office Action for U.S. Appl. No. 16/433,773 mailed Feb. 28, 2025.
Non-Final Office Action for U.S. Appl. No. 17/051,600 mailed Feb. 28, 2025.
Non-Final Office Action for U.S. Appl. No. 17/394,055 mailed Mar. 13, 2025.
Non-Final Office Action for U.S. Appl. No. 17/394,055 mailed Mar. 19, 2025.
Non-Final Office Action for U.S. Appl. No. 17/446,654 mailed May 1, 2025.
Non-Final Office Action for U.S. Appl. No. 17/595,747 mailed Jun. 12, 2025.

(56)            References Cited

OTHER PUBLICATIONS

Non-Final Office Action for U.S. Appl. No. 17/631,619 mailed Mar. 19, 2025.
Non-Final Office Action for U.S. Appl. No. 17/645,821 mailed Mar. 31, 2025.
Non-Final Office Action for U.S. Appl. No. 17/653,314 mailed May 8, 2025.
Non-Final Office Action for U.S. Appl. No. 17/655,464 mailed Mar. 20, 2025.
Non-Final Office Action for U.S. Appl. No. 17/664,487 mailed May 19, 2025.
Non-Final Office Action for U.S. Appl. No. 17/754,736 mailed Mar. 31, 2025.
Non-Final Office Action for U.S. Appl. No. 17/756,201 mailed Apr. 24, 2025.
Non-Final Office Action for U.S. Appl. No. 17/758,152 mailed Apr. 8, 2025.
Non-Final Office Action for U.S. Appl. No. 17/809,083 mailed Apr. 2, 2025.
Non-Final Office Action for U.S. Appl. No. 17/809,083 mailed Mar. 7, 2025.
Non-Final Office Action for U.S. Appl. No. 17/878,268 mailed Mar. 17, 2025.
Non-Final Office Action for U.S. Appl. No. 17/912,147 mailed May 29, 2025.
Non-Final Office Action for U.S. Appl. No. 17/929,887 mailed Jun. 25, 2025.
Non-Final Office Action for U.S. Appl. No. 17/930,238 mailed Jun. 30, 2025.
Non-Final Office Action for U.S. Appl. No. 17/996,064 mailed Mar. 6, 2025.
Non-Final Office Action for U.S. Appl. No. 18/003,029 mailed Apr. 18, 2025.
Non-Final Office Action for U.S. Appl. No. 18/006,807 mailed May 29, 2025.
Non-Final Office Action for U.S. Appl. No. 18/042,842 mailed May 22, 2025.
Non-Final Office Action for U.S. Appl. No. 18/043,618 mailed May 19, 2025.
Non-Final Office Action for U.S. Appl. No. 18/164,800 mailed Apr. 25, 2025.
Non-Final Office Action for U.S. Appl. No. 18/247,986 mailed Jun. 4, 2025.
Non-Final Office Action for U.S. Appl. No. 18/264,004 mailed May 15, 2025.
Non-Final Office Action for U.S. Appl. No. 18/265,736 mailed Jul. 1, 2025.
Notice of Allowance for U.S. Appl. No. 17/444,792 mailed Mar. 28, 2025.
Notice of Allowance for U.S. Appl. No. 17/451,345 mailed Jun. 24, 2025.
Notice of Allowance for U.S. Appl. No. 17/596,629 mailed May 27, 2025.
Notice of Allowance for U.S. Appl. No. 17/597,673 mailed Feb. 26, 2025.
Notice of Allowance for U.S. Appl. No. 17/758,316 mailed Mar. 24, 2025.
Notice of Allowance for U.S. Appl. No. 17/996,155 mailed Jun. 24, 2025.
Notice of Allowance for U.S. Appl. No. 17/996,155 mailed Mar. 11, 2025.
Notice of Allowance for U.S. Appl. No. 17/996,253 mailed Apr. 11, 2025.
Notice of Allowance for U.S. Appl. No. 17/996,468 mailed Apr. 14, 2025.
Notice of Allowance for U.S. Appl. No. 18/007,105 mailed Jun. 17, 2025.
Restriction Requirement for U.S. Appl. No. 17/755,236 mailed Apr. 24, 2025.
Restriction Requirement for U.S. Appl. No. 17/929,887 mailed Mar. 10, 2025.
Restriction Requirement for U.S. Appl. No. 17/930,238 mailed Apr. 17, 2025.
Restriction Requirement for U.S. Appl. No. 18/041,109 mailed Jun. 4, 2025.
Restriction Requirement for U.S. Appl. No. 18/150,360 mailed May 19, 2025.
Supplemental Notice of Allowance for U.S. Appl. No. 17/597,673 mailed Apr. 10, 2025.
U.S. Appl. No. 17/596,629, filed Dec. 15, 2021.
U.S. Appl. No. 19/069,480, filed Mar. 4, 2025.
U.S. Appl. No. 19/078,602, filed Mar. 13, 2025.
U.S. Appl. No. 19/092,262, filed Mar. 27, 2025.
U.S. Appl. No. 19/110,938, filed Mar. 12, 2025.
U.S. Appl. No. 19/111,921, filed Mar. 14, 2025.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 63/564,696, filed Mar. 13, 2024.
"Surface Energy Data for Cellulose acetate, CAS # 9004-35-7", Diviersified Enterprises, 2009, 1 page.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.

* cited by examiner

FLUID COLLECTION ASSEMBLIES INCLUDING AT LEAST ONE SHAPE MEMORY MATERIAL DISPOSED IN THE CONDUIT

BACKGROUND

An individual may have limited or impaired mobility such that typical urination processes are challenging or impossible. For example, the individual may have surgery or a disability that impairs mobility. In another example, the individual may have restricted travel conditions such as those experience by pilots, drivers, and workers in hazardous areas. Additionally, fluid collection from the individual may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections.

Thus, users and manufacturers of fluid collection assemblies continue to seek new and improved assemblies, systems, and methods to collect urine.

SUMMARY

Embodiments disclosed herein are related to assemblies, systems, and methods of using fluid collection assemblies and systems. In an embodiment, a fluid collection assembly is disclosed. The fluid collection assembly includes a fluid impermeable barrier at least partially defining a chamber, at least one opening configured to be positioned adjacent to a female urethral opening, and a fluid outlet. The fluid collection assembly also includes at least one porous material disposed in the chamber. Further, the fluid collection assembly includes a conduit extending from the fluid outlet into the chamber, the conduit including one or more walls that define a passageway. Additionally, the fluid collection assembly includes at least one shape memory material at least partially disposed within the one or more walls of the conduit. The at least one shape memory material is sized, shaped, and positioned in the one or more walls to retain a selected geometric configuration.

In an embodiment, a system is disclosed. The system includes a fluid collection assembly. The fluid collection assembly includes a fluid impermeable barrier at least partially defining a chamber, at least one opening configured to be positioned adjacent to a female urethral opening, and a fluid outlet. The fluid collection assembly also includes at least one porous material disposed in the chamber. Further, the fluid collection assembly includes a conduit extending from the fluid outlet into the chamber, the conduit including one or more walls that define a passageway. Additionally, the fluid collection assembly includes at least one shape memory material at least partially disposed within the one or more walls of the conduit. The at least one shape memory material is sized, shaped, and positioned to retain a selected geometric configuration. The system also includes a fluid storage container configured to hold a fluid and a vacuum source fluidly coupled to one or more of the fluid storage container or the fluid collection assembly via the conduit. The vacuum source is configured to remove fluid from the fluid collection assembly via the conduit.

In an embodiment, a method of forming a fluid collection assembly is disclosed. The method includes providing a conduit and at least one shape memory material, the conduit includes one or more walls that define a passageway, the at least one shape memory material at least partially disposed in the one or more walls. The at least one shape memory material is sized, shaped, and positioned to retain a selected geometric configuration. The method also includes positioning at least a portion the conduit through a fluid outlet and into a chamber defined by a fluid impermeable barrier. The fluid impermeable barrier defines at least one opening configured to be positioned adjacent to a female urethral opening. The method also includes positioning at least one porous material in the chamber.

In an embodiment, a method to collect one or more bodily fluids is disclosed. The method includes positioning an opening of a fluid collection assembly adjacent to a female urethral opening. The fluid collection assembly includes a fluid impermeable barrier at least partially defining a chamber, at least one opening configured to be positioned adjacent to a female urethral opening, and a fluid outlet. The fluid collection assembly also includes at least one porous material disposed in the chamber. Further, the fluid collection assembly includes a conduit extending from the fluid outlet into the chamber, the conduit including one or more walls that define a passageway. Additionally, the fluid collection assembly includes at least one shape memory material at least partially disposed within the one or more walls of the conduit. The at least one shape memory material is sized, shaped, and positioned to retain a selected geometric configuration. The method also includes shaping the fluid collection assembly into the selected geometric configuration. The selected geometric configuration is complementary to contours of anatomy of a patient in a region proximate to the female urethral opening. The method further includes receiving fluid from the female urethral opening into a chamber of the fluid collection assembly.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figures 1A, 1B:
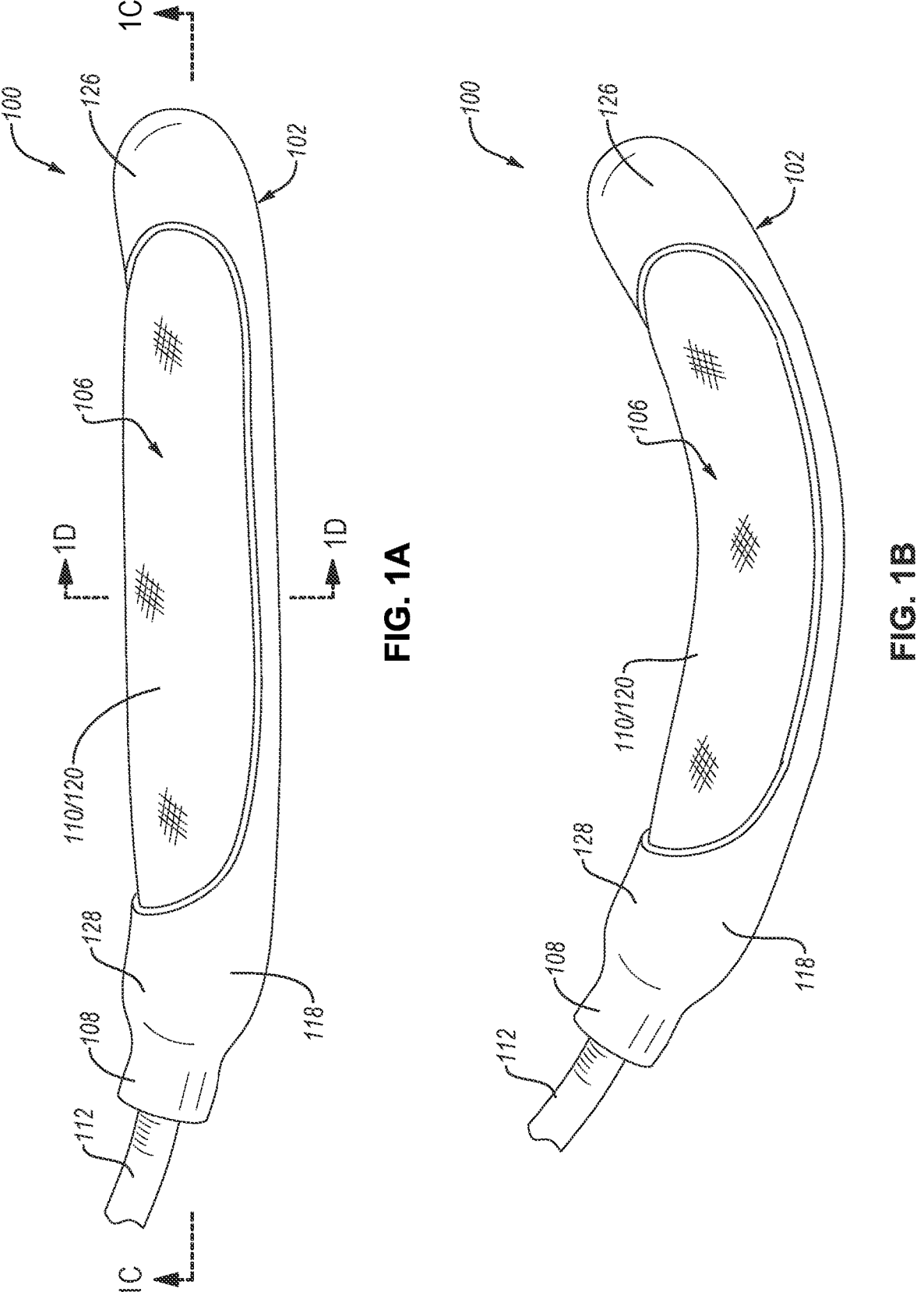
FIGS. 1A and 1B are isometric views of a fluid collection assembly exhibiting a first shape and a second shape, respectively, according to an embodiment.

Embodiments disclosed herein are related to assemblies, systems, and methods of using fluid collection assemblies and systems. The assemblies, systems, and methods of using fluid collection assemblies and systems include at least one shape memory material for forming and maintaining the fluid collection assembly into a selected shape. The shape memory material may enable for selective manipulation of the fluid collection assembly to contour to the anatomical features of variously sized patients.

The fluid collection assemblies disclosed herein include a fluid impermeable barrier. The fluid impermeable barrier at least defines a chamber, at least one opening extending therethrough that is configured to be positioned adjacent to a female urethral opening, and a fluid outlet. The fluid collection assemblies disclosed herein may include at least one porous material disposed in the chamber and a conduit at least partially disposed in the chamber (e.g., extending through the fluid outlet). The fluid collection assemblies disclosed herein include at least one shape memory material at least partially disposed in the conduit.

During use, the female fluid collection assembly is disposed with the opening of the fluid collection assembly adjacent to a urethral opening of a female patient. The urethral opening may discharge one or more bodily fluids, such a urine, blood, or sweat. The bodily fluids may be received by the porous material and wicked away from the urethral opening and into the chamber. The bodily fluids may be removed from the chamber via a fluid outlet defined by the fluid impermeable barrier. For example, a suction force may be applied to a conduit that is at least partially disposed in the fluid outlet and the suction force may pull the bodily fluids into the conduit and out of the chamber.

Some of the bodily fluids that are discharged from the urethral opening may leak from the chamber. The leaked bodily fluids may cause patient (e.g., an individual using the fluid collection assembly) discomfort, embarrassment, and create unsanitary conditions that require cleaning. Poor fit between the female fluid collection assembly and the region about the urethral opening may cause the bodily fluids to leak from the female fluid collection assembly. For example, the poor fit may cause gaps to be present between the porous material that extends across the opening and the region about the urethral opening. These gaps may provide locations through which the bodily fluids may flow without being received by the porous material and/or locations at which bodily fluids may leave the porous material. To minimize formation of gaps between the porous material and the urethral opening, conventional fluid collection assemblies (e.g., fluid collection assemblies without a shape memory material) may be manipulated (e.g., bent or otherwise shaped) to match the anatomical shape of the patient to conform to the shape of the vaginal region of the patient. Conventional fluid collection assemblies rely on contact between the thighs of the patient and the conventional fluid collection assemblies to maintain the shape of the conventional fluid collection assemblies. However, movement by the patient, thin patients, young patients, and forgetful patients (e.g., patients with dementia) may have issues maintaining contact between the thighs and the conventional fluid collection assemblies. As such, movement by the patient, thin patients, young patients, and forgetful patients may cause the conventional fluid collection assemblies to change a shape thereof which, in turn, may form gaps through which the bodily fluids may leak.

The shape of the fluid collection assemblies disclosed herein may be manipulated into a selected shape to provide a more comfortable and effective fit on the patient. The shape memory material of the fluid collection assemblies disclosed herein may at least temporarily maintain the fluid collection assemblies in a selected shape. By shaping and maintaining the shape of the fluid collection assembly with the shape memory material to match the anatomical shape of the patient, more of the fluid may be collected and retained in the fluid collection assembly. For example, shaping the fluid collection assembly to match the anatomical shape of the patient inhibits the fluid collection assembly from moving away from the groin of the patient (e.g., when the patient moves). Moving the fluid collection assembly away from the patient increases the likelihood that the bodily fluids leak from the fluid collection assembly during use. As such, shaping the fluid collection assembly with the shape memory material to match the anatomical shape of the wear minimizes leaks.

Figures 1C, 1D:
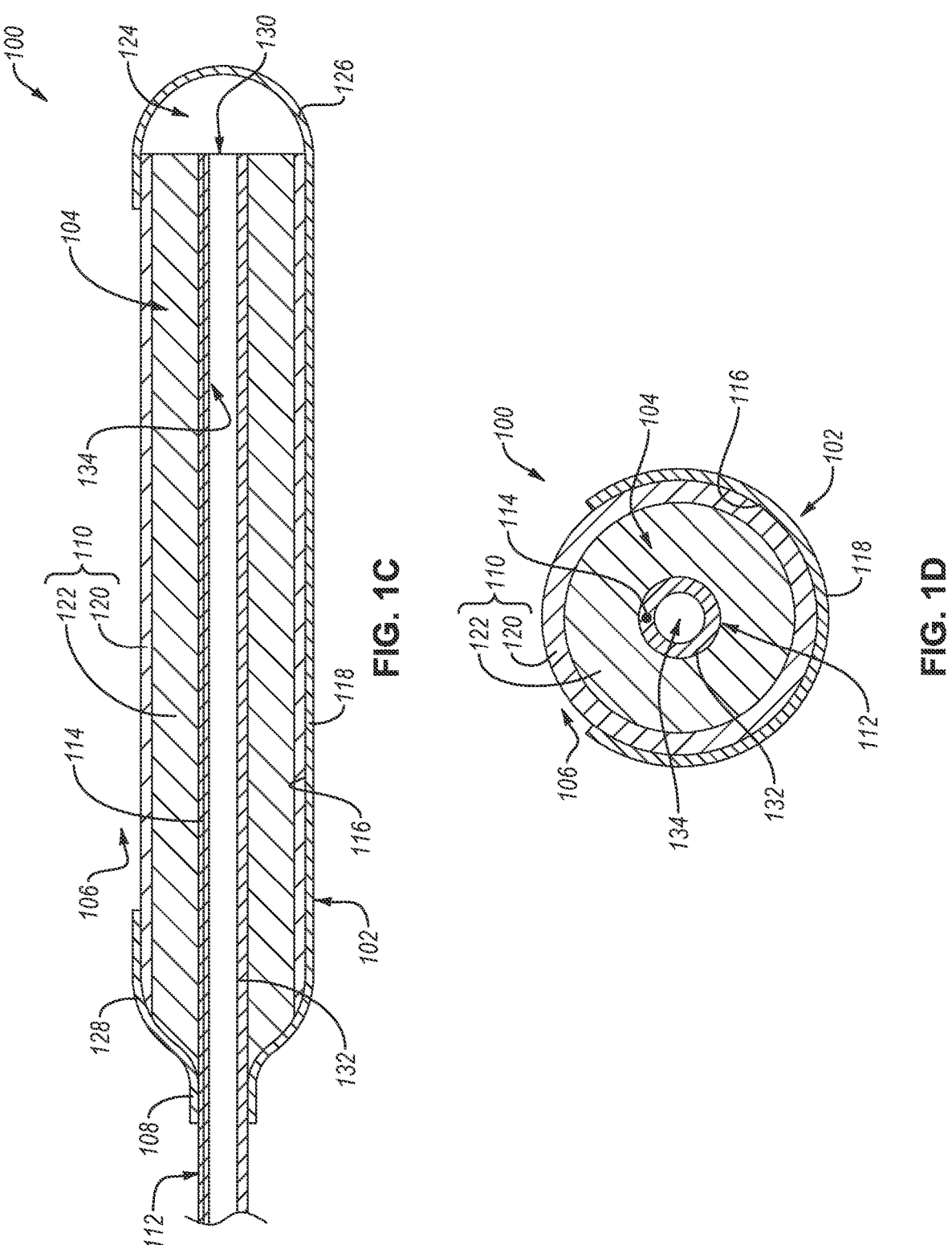
FIGS. 1C and 1D are cross-sectional schematics of the fluid collection assembly shown in FIG. 1B taken along planes 1C-1C and 1D-1D, respectively.

FIGS. 1A and 1B are isometric views of a fluid collection assembly 100 exhibiting a first shape and a second shape, respectively, according to an embodiment. FIGS. 1C and 1D are cross-sectional schematics of the fluid collection assembly 100 shown in FIG. 1B taken along planes 1C-1C and 1D-1D, respectively. The fluid collection assembly 100 is an example of a female fluid collection assembly 100 for receiving and collection bodily fluids from a female patient. The fluid collection assembly 100 includes a fluid impermeable barrier 102 that defines at least a chamber 104, at least one opening 106, and a fluid outlet 108. The fluid collection assembly 100 also includes at least one porous material 110 (e.g., wicking material) disposed in the chamber 104. The fluid collection assembly 100 further includes at least one conduit 112 at least partially disposed within the chamber 104 and at least one shape memory material 114 at least partially disposed within the conduit 112.

The fluid impermeable barrier 102 at least partially defines a chamber 104 (e.g., interior region) and an opening 106. For example, the interior surface(s) 116 of the fluid impermeable barrier 102 at least partially defines the chamber 104 within the fluid collection assembly 100. The fluid impermeable barrier 102 temporarily stores bodily fluids in the chamber 104. The fluid impermeable barrier 102 may be formed of any suitable fluid impermeable material(s), such as a fluid impermeable polymer (e.g., silicone, polypropylene, polyethylene, polyethylene terephthalate, a polycarbonate, etc.), a metal film, natural rubber, another suitable material, or combinations thereof. As such, the fluid impermeable barrier 102 substantially prevents the bodily fluids from passing through the fluid impermeable barrier 102. In an example, the fluid impermeable barrier 102 may be air permeable and fluid impermeable. In such an example, the fluid impermeable barrier 102 may be formed of a hydrophobic material that defines a plurality of pores. At least one or more portions of at least an outer surface 118 of the fluid impermeable barrier 102 may be formed from a soft and/or smooth material, thereby reducing chaffing.

In some examples, the fluid impermeable barrier 102 may be tubular (ignoring the opening), such as substantially cylindrical (as shown), oblong, prismatic, or flattened tubes. During use, the outer surface 118 of the fluid impermeable barrier 102 may contact the patient. The fluid impermeable barrier 102 may be sized and shaped to fit in the gluteal cleft between the legs of a female patient.

The opening 106 provides an ingress route for fluids to enter the chamber 104. The opening 106 may be defined by the fluid impermeable barrier 102 such as by an inner edge of the fluid impermeable barrier 102. For example, the opening 106 is formed in and extends through the fluid impermeable barrier 102, from the outer surface 118 to the inner surface 116, thereby enabling the bodily fluids to enter the chamber 104 from outside of the fluid collection assembly 100. The opening 106 may be an elongated hole in the fluid impermeable barrier 102. For example, the opening 106 may be defined as a cut-out in the fluid impermeable barrier 102. The opening 106 may be located and shaped to be positioned adjacent to a female urethral opening.

The fluid collection assembly 100 may be positioned proximate to the female urethral opening and urine may enter the chamber of the fluid collection assembly 100 via the opening 106. The fluid collection assembly 100 is configured to receive the bodily fluids into the chamber 104 via the opening 106. When in use, the opening 106 may have an elongated shape that extends from a first location below the urethral opening (e.g., at or near the anus or the vaginal opening) to a second location above the urethral opening (e.g., at or near the top of the vaginal opening or the mons pubis).

The opening 106 may have an elongated shape because the space between the legs of a female is relatively small when the legs of the female are closed, thereby only permitting the flow of the bodily fluids along a path that corresponds to the elongated shape of the opening 106 (e.g., longitudinally extending opening). The opening 106 in the fluid impermeable barrier 102 may exhibit a length that is measured along the longitudinal axis of the fluid collection assembly 100 that may be at least about 10% of the length of the fluid collection assembly 100, such as about 25% to about 50%, about 40% to about 60%, about 50% to about 75%, about 65% to about 85%, or about 75% to about 95% of the length of the fluid collection assembly 100.

The opening 106 in the fluid impermeable barrier 102 may exhibit a width that is measured transverse to the longitudinal axis of the fluid collection assembly 100 that may be at least about 10% of the circumference of the fluid collection assembly 100, such as about 25% to about 50%, about 40% to about 60%, about 50% to about 75%, about 65% to about 85%, or about 75% to about 100% of the circumference of the fluid collection assembly 100. The opening 106 may exhibit a width that is greater than 50% of the circumference of the fluid collection assembly 100 since the vacuum (e.g., suction) through the conduit 112 pulls the fluid through the porous material 110 and into the conduit 112. In some examples, the opening 106 may be vertically oriented (e.g., having a major axis parallel to the longitudinal axis of the assembly 100). In some examples (not shown), the opening 106 may be horizontally oriented (e.g., having a major axis perpendicular to the longitudinal axis of the assembly 100). In an example, the fluid impermeable barrier 102 may be configured to be attached to the patient, such as adhesively attached (e.g., with a hydrogel adhesive) to the patient. According to an example, a suitable adhesive is a hydrogel layer.

In some examples, the fluid impermeable barrier 102 may define an fluid outlet 108 sized to receive the conduit 112. The at least one conduit 112 may be disposed in the chamber 104 via the fluid outlet 108. The fluid outlet 108 may be sized and shaped to form an at least substantially fluid tight seal against the conduit 112 or the at least one tube, thereby substantially preventing the bodily fluids from escaping the chamber 104.

The fluid impermeable barrier 102 may include markings (not shown) thereon, such as one or more markings to aid a patient in aligning the assembly 100 on the patient. For example, a line on the fluid impermeable barrier 102 (e.g., opposite the opening 106) may allow a healthcare professional to align the opening 106 over the urethral opening of the patient. In examples, the markings may include one or more of alignment guide or an orientation indicator, such as a stripe or hashes. Such markings may be positioned to align the assembly 100 to one or more anatomical features such as a pubic bone, etc.

The fluid collection assembly 100 includes porous material 110 disposed in the chamber 104. The porous material 110 may cover at least a portion (e.g., all) of the opening 106. The porous material 110 is exposed to the environment outside of the chamber 104 through the opening 106. The porous material 110 may be configured to move any fluid away from the opening 106, thereby preventing the fluid from escaping the chamber 104. The permeable properties referred to herein may be wicking, capillary action, diffusion, or other similar properties or processes, and are referred to herein as "permeable" and/or "wicking." Such "wicking" may not include absorption of fluid into the porous material. Put another way, substantially no absorption of fluid into the material may take place after the material is exposed to the fluid and removed from the fluid for a time. While no absorption is desired, the term "substantially no absorption" may allow for nominal amounts of absorption of fluid into the porous material (e.g., absorbency), such as less than about 30 wt % of the dry weight of the porous material, less than about 20 wt %, less than about 15 wt %, less than about 10 wt %, less than about 7 wt %, less than about 5 wt %, less than about 3 wt %, less than about 2 wt %, less than about 1 wt %, or less than about 0.5 wt % of the dry weight of the porous material. The porous material 110 may also wick the fluid generally towards an interior of the chamber 104, as discussed in more detail below. The porous material 110 may include one or more of a fluid permeable membrane 120 or a fluid permeable support 122. However, in some embodiments, it is noted that the porous material 110 may include an absorption material (e.g., hydrophilic material) instead of a wicking material.

The fluid collection assembly 100 may include the fluid permeable membrane 120 disposed in the chamber 104. The fluid permeable membrane 120 may cover at least a portion (e.g., all) of the opening 106. The fluid permeable membrane 120 may be composed to wick fluid away from the opening 106, thereby preventing the fluid from escaping the chamber 104.

The fluid permeable membrane 120 may include any material that may wick the fluid. For example, the fluid permeable membrane 120 may include fabric, such as a gauze (e.g., a silk, linen, or cotton gauze), another soft fabric, or another smooth fabric. Forming the fluid permeable membrane 120 from gauze, soft fabric, and/or smooth fabric may reduce chaffing caused by the fluid collection assembly 100.

The fluid collection assembly 100 may include the fluid permeable support 122 disposed in the chamber 104. The fluid permeable support 122 is configured to support the fluid permeable membrane 120 since the fluid permeable membrane 120 may be formed from a relatively foldable, flimsy, or otherwise easily deformable material. For example, the fluid permeable support 122 may be positioned such that the fluid permeable membrane 120 is disposed between the fluid permeable support 122 and the fluid impermeable barrier 102. As such, the fluid permeable support 122 may support and maintain the position of the fluid permeable membrane 120. The fluid permeable support 122 may include any material that may wick the fluid, such as any of the fluid permeable membrane materials disclosed herein above. For example, the fluid permeable membrane material(s) may be utilized in a more dense or rigid form than in the fluid permeable membrane 120 when used as the fluid permeable support 122. The fluid permeable support 122 may be formed from any fluid permeable material that is less deformable than the fluid permeable membrane 120. For example, the fluid permeable support 122 may include a porous polymer (e.g., nylon, polyester, polyurethane, polyethylene, polypropylene, etc.) structure or an open cell foam, such as spun nylon fibers. In some examples, the fluid permeable support 122 may be formed from a natural material, such as cotton, wool, silk, or combinations thereof. In such examples, the material may have a coating to prevent or limit absorption of fluid into the material, such as a water repellent coating. In some examples, the fluid permeable support 122 may be formed from fabric, felt, gauze, or combinations thereof. In some examples, the fluid permeable membrane 120 may be optional. For example, the porous material 110 may include only the fluid permeable support 122. In some examples, the fluid permeable support 122 may be optionally omitted from the fluid collection assembly 100. For example, the porous material 110 may only include the fluid permeable membrane 120.

The fluid permeable support 122 may have a greater ability to wick fluids than the fluid permeable membrane 120, such as to move the fluid inwardly from the outer surface of the fluid collection assembly 100. In some examples, the wicking ability of the fluid permeable support 122 and the fluid permeable membrane 120 may be substantially the same.

The fluid permeable membrane 120 and the fluid permeable support 122 may at least substantially completely fill the portions of the chamber 104 that are not occupied by the conduit 112. In some examples, the fluid permeable membrane 120 and the fluid permeable support 122 may not substantially completely fill the portions of the chamber 104 that are not occupied by the conduit 112. In such an example, the fluid collection assembly 100 includes the fluid reservoir 124 (FIG. 1C) disposed in the chamber 104.

The fluid reservoir 124 is a substantially unoccupied portion of the chamber 104. The fluid reservoir 124 may be defined between the fluid impermeable barrier 102 and one or both of the fluid permeable membrane 120 and fluid permeable support 122. The bodily fluids that are in the chamber 104 may flow through the fluid permeable membrane 120 and/or fluid permeable support 122 to the fluid reservoir 124. The fluid reservoir 124 may retain of the bodily fluids therein.

The bodily fluids that are in the chamber 104 may flow through the fluid permeable membrane 120 and/or fluid permeable support 122 to the fluid reservoir 124. The fluid impermeable barrier 102 may retain the bodily fluids in the fluid reservoir 124. While depicted at the distal end region 126, the fluid reservoir 124 may be located in any portion of the chamber 104 such as the proximal end region 128. The fluid reservoir 124 may be located in a portion of the chamber 104 that is designed to be located in a gravimetrically low point of the fluid collection assembly when the assembly is worn.

In some examples (not shown), the fluid collection assembly 100 may include multiple reservoirs, such as a first reservoir that is located at the portion of the chamber 104 closest to the inlet 130 (e.g., distal end region 126) and a second reservoir that is located at the portion of the of the chamber 104 that is closest to the outlet of the conduit 112 (e.g., proximal end region 128). In another example, the fluid permeable support 122 is spaced from at least a portion of the conduit, and the fluid reservoir 124 may be the space between the fluid permeable support 122 and the conduit.

The conduit 112 includes one or more walls 132 defining a passageway 134. The conduit 112 may be at least partially disposed in the chamber 104. The conduit 112 may be used to remove bodily fluids from the chamber 104. The conduit 112 (e.g., a tube) includes an inlet 130 and an outlet positioned downstream from the inlet 130. The outlet may be operably coupled to a suction source, such as a vacuum pump for withdrawing fluid form the chamber through the conduit 112. For example, the conduit 112 may extend into the fluid impermeable barrier 102 from the proximal end region 128 and may extend to the distal end region 126 to a point proximate to the fluid reservoir 124 therein such that the inlet 130 is in fluid communication with the fluid reservoir 124. The conduit 112 fluidly couples the chamber 104 with the fluid storage container (not shown) or the vacuum source (not shown).

The conduit 112 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some examples, the conduit 112 may include silicon or latex. In some examples, the conduit 112 may include one or more portions that are resilient, such as to by having one or more of a diameter or wall thickness that allows the conduit to be flexible.

As shown in FIG. 1C, the end of the conduit 112 may extend through a bore in the fluid permeable membrane 120 and/or fluid permeable support 122, such as into the fluid reservoir 124. For example, the inlet 130 may be extend into or be positioned in the fluid reservoir 124. In the illustrated embodiment, the conduit 112 is at least partially disposed in the fluid reservoir 124. In some examples (not shown), the conduit 112 may enter the chamber 104 in the distal end region 126 and the inlet 130 of the conduit 112 may be disposed in the distal end region 126 (e.g., in the fluid reservoir 124). The fluid collected in the fluid collection assembly 100 may be removed from the chamber 104 via the conduit 112.

In some examples, the inlet 130 may not extend into the fluid reservoir 124. In such examples, the inlet 130 may be disposed within the porous material 110 (fluid permeable membrane 120 and/or fluid permeable support 122) or at a terminal end thereof. For example, an end of the conduit 112 may be coextensive with or recessed within the fluid permeable membrane 120 and/or fluid permeable support 122.

Locating the inlet 130 at or near a location expected to be the gravimetrically low point of the chamber 104 when worn by a patient enables the conduit 112 to receive more of the bodily fluids than if the inlet 130 was located elsewhere and reduces the likelihood of pooling (e.g., pooling of the bodily fluids may cause microbe growth and foul odors). For instance, the bodily fluids in the fluid permeable membrane 120 and the fluid permeable support 122 may flow in any direction due to capillary forces. However, the bodily fluids may exhibit a preference to flow in the direction of gravity, especially when at least a portion of the fluid permeable membrane 120 and/or the fluid permeable support 122 is saturated with the bodily fluids. Accordingly, one or more of the inlet 130 or the fluid reservoir 124 may be located in the fluid collection assembly in a position expected to be the gravimetrically low point in the fluid collection assembly when worn by a patient, such as the distal end region 126.

In an example, the conduit 112 is configured to be at least insertable into the chamber 104. In such an example, the conduit 112 may include one or more markers (not shown) on an exterior thereof that are located to facilitate insertion of the conduit 112 into the chamber 104. For example, the conduit 112 may include one or more markings thereon that are configured to prevent over or under insertion of the conduit 112, such as when the conduit 112 defines an inlet 130 that is configured to be disposed in or adjacent to the fluid reservoir 124. In another example, the conduit 112 may include one or more markings thereon that are configured to facilitate correct rotation of the conduit 112 relative to the chamber 104. The one or more markings may include a line, a dot, a sticker, or any other suitable marking.

Figure 8:
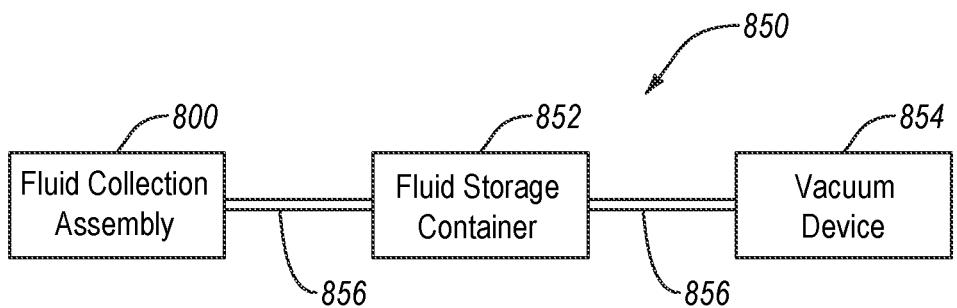
FIG. 8 is a block diagram of a system for fluid collection, according to an embodiment.

As described in more detail below, the conduit 112 is configured to be coupled to, and at least partially extend between, one or more of the fluid storage container (not shown) and the vacuum source (FIG. 8). In an example, the conduit 112 is configured to be directly connected to the vacuum source. In such an example, the conduit 112 may extend from the fluid impermeable barrier 102 by at least one foot, at least two feet, at least three feet, or at least six feet. In another example, the conduit 112 is configured to be indirectly connected to at least one of the fluid storage container (FIG. 8) and the vacuum source. In some examples, the conduit is secured to a patient's skin with a catheter securement assembly, such as a STATLOCK® catheter securement assembly available from C. R. Bard, Inc., including but not limited to those disclosed in U.S. Pat. Nos. 6,117,163; 6,123,398; and 8,211,063, the disclosures of which are all incorporated herein by reference in their entirety.

The inlet 130 and the outlet 112 are configured to fluidly couple (e.g., directly or indirectly) the vacuum source (not shown) to the chamber 104 (e.g., the fluid reservoir 124). As the vacuum source (FIG. 8) applies a vacuum/suction in the conduit 112, the bodily fluids in the chamber 104 (e.g., at the distal end region 126, such as in the fluid reservoir 124) may be drawn into the inlet 130 and out of the fluid collection assembly 100 via the conduit 112. In some examples, the conduit may be frosted or opaque (e.g., black) to obscure visibility of the bodily fluids therein.

The fluid collection assembly 100 includes a shape memory material 114 at least partially disposed in the walls 132 of the conduit 112. The shape memory material may be sized, shaped, and positioned in the fluid collection assembly 100 to cause at least a portion of the fluid collection assembly 100 to retain a selected shape (e.g., geometric configuration). In an embodiment, the shape memory material 114 is configured to be bent, shaped, or otherwise deformed (hereafter collectively referred to as "shape," "shaped," or "shaping"). In an example, the shape memory material 114 is configured to be shaped along an entire length thereof. Allowing the shape memory material 114 to be shaped along the entire length thereof may allow the fluid collection assembly 100 to exhibit a shape that substantially corresponds to the anatomical features of the patient. For example, the shape memory material 114 may exhibit a first (e.g., initial) shape. The fluid collection assembly 100 may exhibit the first configuration (i.e., a generally linear shape shape) illustrated in FIG. 1A when the shape memory material 114 exhibits the first shape (e.g., a generally straight shape). The shape memory material 114 may be shaped to exhibit a second shape that is different than the first shape. The fluid collection assembly 100 may exhibit the second configuration (e.g., a generally curved shape) illustrated in FIG. 1B when the shape memory material 114 exhibits the second shape. The second configuration of the fluid collection assembly 100 may better correspond to the shape of the region about the urethral opening than the first configuration.

In an example, the shape memory material 114 is configured to be shaped at one or more selected location thereof. In such an example, the selected locations of the shape memory material 114 may be preferentially shaped relative to the rest of the shape memory material 114. While configuring the shape memory material 114 to be shaped at the selected location may inhibit the fluid collection assembly 100 from exhibiting a shape that substantially corresponds to the anatomical features of the patient, it may facilitate shaping of the fluid collection assembly 100, especially for less experienced medical individuals (e.g., medical practitioners or patients). In an embodiment, the shape memory material 114 may not be configured to be shaped. Instead, the shape memory material may exhibit a selected shape that corresponds or substantially corresponds to the anatomical feature of the patient. In such an embodiment, the shape memory material 114 may be more rigid and/or resilient than the rest of the fluid collection assembly 100 thereby causing at least a portion of the fluid collection assembly 100 to correspond to the selected shape of the shape memory material 114.

The shape memory material 114 may include a shape memory polymer or a metal (e.g., shape memory metal). Generally, the shape memory material 114 is composed to adopt an intermediate or permanent shape in response to a stimuli. For example, the shape memory material 114 may exhibit a first (e.g., initial) shape and may be switched from the first shape to a second shape by the stimuli, wherein the second shape is different than the first shape. The shape memory material 114 may also be switched from the second shape back to the first shape or a third shape that is different than the first and second shapes in response to the stimuli.

The stimuli may include an external physical force (e.g., bending force), heat, electrical bias, or a magnetic field. While the term "shape memory" is used to describe some of the "shape memory materials" herein, it should be understood that, in some examples, the material modified by the term "shape memory" may not necessarily need to return to a preselected shape upon application of a stimuli, as understood as the classical definition of the "shape memory material." Rather, at least some of the shape memory materials disclosed herein may simply hold a selected shape when bent, set, or cured into a specific shape and/or when cooled in a specific shape, regardless of the stimuli applied thereto after. The shape memory materials may be returned to the original shape or changed to a new shape by application of stimuli. For example, a metal wire bent to a first shape may be utilized as the shape memory material 114, whereinafter the metal wire may be modified to a second shape via physical force applied thereto or via heating. However, in some embodiments, the shape memory material 114 may exhibit a selected shape, as discussed above and application of the stimuli may cause the shape memory material to deform (e.g., elastically deform or bend) into an intermediate shape. In such embodiments, the shape memory material 114 may return to the first initial shape upon removal of the stimuli such that the shape memory material 114 does not maintain the intermediate shape.

In an embodiment, the shape memory material 114 may include metal, such as an elemental metal, an alloy, or shape memory alloy. Suitable shape memory metals may include aluminum, silver, copper, iron, nickel, zinc, tin, beryllium, or the like. Suitable shape memory alloys may include standard steels, stainless steel, carbon alloy steel, head treated steel, galvanized steel, aluminum alloys, nickel-titanium alloys (e.g., Nitinol, Ni—Ti—Cu, Ni—Ti, Co, or the like), copper-based alloys (e.g., Cu—Zn—Al, Cu—Al—Ni, Cu—Al—Sn, or the like), Co—Cr—Ni—Mo alloys (e.g., Elgiloy® or the like), or any other alloy having shape memory characteristics. As explained above, the shape memory metals or alloys may merely be metals or alloys that may be shaped to a selected configuration. In some examples, the shape memory metals or alloys may return to a primary shape when an external stimuli is applied thereto. In some examples, the outer surface of the shape memory metal may be coated with a polymer, anodized, passivated, or otherwise treated to prevent corrosion.

Shape memory polymers ("SMPs") may include polyurethane-based SMPs such as a copolymer (e.g., copolyester, polyurethane, polyetherester, etc.) including blocks of one or more of poly(ε-caprolactone), polyethyleneterephthalate (PET), polyethyleneoxide (PEO), polyethylene glycol (PEG), polystyrene, polymethylmethacrylate (PMMA), Polybutylmethacrylate (PBMA), poly(N,N-butadiene), poly (N-methyl-N-oxazoline), polytetrahydrofuran, or poly(butylene terephthalate); thermoplastic polymers such as polyether ether ketone (PEEK), nylon, acetal, polytetrafluoroethylene (PTFE), polypropylene, polyethylene, acrylonitrile butadiene styrene (ABS), polysulphone, or the like; Polynorbonene; other deformable polymers; or any other shape memory polymer.

The shape memory material 114 is distinct from the walls 132 of the conduit 112. The shape memory material 114 is distinct from the walls 132 of the conduit 112 when the shape memory material 114 is formed from a material that is different than the walls 132 or is otherwise distinguishable from the walls 132. When the shape memory material 114 is distinct from the walls 132 of the conduit 112, the shape memory material 114 may be disposed in selected regions of the conduit 112 rather than dispersed through the conduit 112. This allows the conduit 112 to be formed from a greater variety of materials since the materials that form the conduit 112 do not need to exhibit the properties of the shape memory material 114.

In an embodiment, the shape memory material 114 includes at least one wire (e.g., at least one rod). The wire includes a length measured along a longitudinal axis of the wire, a width measured perpendicularly to the length and a thickness measured perpendicularly to the length and the width. The length of the wire is significantly greater than the width and the thickness. In an embodiment, the shape memory material 114 includes a plate (e.g., strip). The plate exhibits a length, a width, and a thickness. The width of the plate is greater (e.g., at least 50% greater) than the thickness. The plate may initially (i.e., before shaping the plate) exhibit one or more bends therein (e.g., the plate is an at least partial tube). For example, as illustrated, the plate may exhibit a bend in the direction that is parallel to the width. The bend in the plate may be configured to correspond to the shape of the conduit 112. However, the bend in the plate may make shaping the plate more difficult. In an embodiment, the plate may be substantially planar.

As shown in FIGS. 1C and 1D, the shape memory material 114 may be at least partially disposed within the one or more walls 132 of the conduit 112. In an example, the shape memory material 114 is completely surrounded by the conduit 112 (e.g., completely disposed with the walls 132). Completely surrounding the shape memory material 114 with the conduit 112 makes it more difficult for the shape memory material 114 from becoming dislodged from the conduit 112 than if the shape memory material 114 is only partially disposed in the conduit 112. In an example, only a portion of the shape memory material 114 is surrounded by the conduit 112.

The walls 132 of the conduit 112 may exhibit a thickness measured perpendicular to a longitudinal axis of the conduit 112 (e.g., measured parallel to a radius of the conduit 112). In an embodiment, the thickness of the conduit 112 may be greater than about 0.75 mm, such as greater than about 1 mm, greater than about 1.25 mm, greater than about 1.5 mm, greater than about 1.75 mm, greater than about 2 mm, or in ranges of about 0.75 mm to about 1.25 mm, about 1 mm to about 1.5 mm, about 1.25 mm to about 1.75 mm, about 1.5 mm to about 2 mm, or about 1.75 mm to about 2.25 mm. The shape memory material 114 exhibits a thickness measure parallel to the thickness of the conduit 112. In an embodiment, the thickness of the shape memory material 114 is less than a thickness of the walls 132 of the conduit 112 which may allow the shape memory material 114 to be completely disposed in the wall 132 or, at least, improve adhesion between the walls 132 and the conduit 112. In such an embodiment, depending on the thickness of the walls 132, the shape memory material 114 may exhibit a thickness that about 0.25 mm or less, about 0.5 mm or less, about 0.75 mm or less, about 1 mm or less, about 1.5 mm or less, about 1.75 mm or less, or in ranges of about 0.25 mm to about 0.75 mm, about 0.5 mm to about 1 mm, about 0.75 mm to about 1.25 mm, about 1 mm to about 1.5, about 1.25 mm to about 1.75 mm, or about 1.5 mm to about 2 mm. It is noted that the thickness of the shape memory material 114 may be greater than about 1.75 mm, depending on the thickness of the walls 132. The thickness of the shape memory material 114 may be about 95% or less the thickness of the conduit 112, such as in ranges of about 30% to about 50%, about 40% to about 60%, about 50% to about 70%, about 60% to about 80%, or about 70% to about 90%. Generally, increasing the thickness of the shape memory material 114 may increase the ability of the shape memory material 114 to maintain a shape thereof but also increases the likelihood that the shape memory material 114 becomes dislodged from the conduit 112. As such, the thickness of the shape memory material 114 relative to the thickness of the walls 132 may be selected based on whether the ability of the shape memory material 114 to maintain its shape or prevent the shape memory material 114 becoming dislodged is preferred. In an embodiment, the thickness of the shape memory material 114 may be greater than a thickness of the walls 132, such as when the shape memory material 114 is only partially disposed in the conduit 112 and the ability of the shape memory material 114 to maintain its shape is preferred.

Disposing the shape memory material 114 in the conduit 112 may inhibit the shape memory material 114 from protruding out of the fluid impermeable barrier 102, which may cause patient discomfort and cut the skin of that patient. For example, to protrude out of the fluid impermeable barrier 102, the shape memory material 114 must become dislodged from the conduit 112, a length of the shape memory material 114 that becomes dislodged must exhibit a length that is sufficient to extend through the porous material 110, and penetrate through the fluid impermeable barrier 102. Dislodging the shape memory material 114, let alone dislodging a length of the shape memory material 114 from the conduit 112 that is sufficient to extend through the porous material 110, may be difficult, especially when the shape memory material 114 is completely disposed in the conduit 112 since it requires rupturing a portion of the conduit 112. Further, it may be difficult for the shape memory material 114 to penetrate through the fluid impermeable barrier 102. However, it is noted that the shape memory material 114 may include a terminal end that is sharp (e.g., due to cutting the shape memory material 114) which may facilitate the shape memory material 114 penetrating the fluid impermeable barrier 102. All of this makes it difficult for the shape memory material 114 to protrude from the fluid impermeable barrier 102 when the shape memory material 114 is at least partially disposed in the conduit 112, even when the fluid collection assembly 100 is mishandled.

In particular, disposing the shape memory material 114 at least partially in the conduit 112 may decrease the likelihood that the shape memory material 114 protrudes from the fluid impermeable barrier 102 than if the shape memory material 114 is disposed in other portions of the fluid collection assembly 100 (e.g., within the fluid impermeable barrier 102, between the fluid impermeable barrier 102 and the porous material 110, within the porous material 110, or between the porous material 110 and the conduit 112). For example, not disposing the shape memory material 114 in the conduit 112 eliminates the pre-requisite that the shape memory material 114 must be at least partially dislodged from the conduit 112 before the shape memory material 114 may protrude from the fluid impermeable barrier 102. Thus, not disposing the shape memory material 114 in the conduit 112 increases the likelihood that the shape memory material 114 protrudes from the fluid impermeable barrier 102.

In some embodiments, excluding the shape memory material 114, the conduit 112 may be the most rigid material in the fluid collection assembly 100 which makes the conduit 112 difficult to shape when the shape memory material 114 is spaced from the conduit 112. For example, when the shape memory material 114 is space from the conduit 112, the shape of the conduit 112 is only changed when the porous material 110 presses against the conduit 112. Pressing the porous material 110 against the conduit 112 to change the shape of the conduit 112 causes a compressive force to be applied to the porous material 110 which decreases the quantity of bodily fluids that may be stored in the porous material 110. However, at least partially disposing the shape memory material 114 in the conduit 112 causes the shape memory material 114 to control the shape of the conduit 112 instead of the porous material 110 pressing against the conduit 112. This decreases the compressive force that is applied to the porous material 110 thereby increasing the quantity of bodily fluids that may be stored in the porous material 110. The increased quantity of bodily fluids that may be stored in the porous material 110 decreases the likelihood that the porous material 110 becomes saturated with and leaks the bodily fluids.

In an embodiment, the fluid collection assembly 100 may include at least one shape memory material that is not at least partially disposed in the conduit 112 in addition to the shape memory material 114 that is at least partially disposed in the conduit 112. Examples of shape memory materials that are not disposed in the conduit 112 are disclosed in PCT International App. No. WO 2021/016026 filed on Jul. 16, 2020, the disclosure of which is incorporated herein, in its entirety, by this references.

Other embodiments of fluid impermeable barriers, fluid permeable membranes, fluid permeable supports, chambers, and their shapes and configurations are disclosed in U.S. Pat. No. 10,973,678 filed on Jun. 2, 2017; U.S. Pat. No. 10,390,989 filed on Sep. 8, 2016; and U.S. Pat. No. 10,225,376 filed on Jun. 1, 2017, the disclosure of each of which is incorporated herein, in its entirety, by this reference.

Figure 2A:
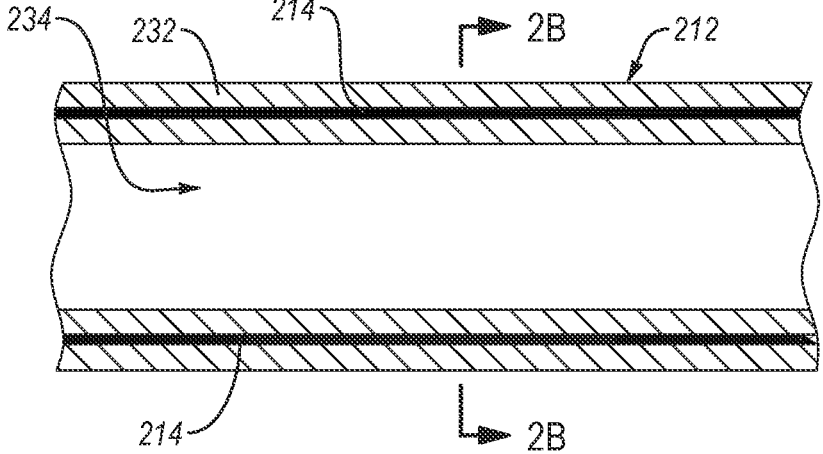
FIG. 2A is a cross-sectional schematic of a conduit that includes a plurality of shape memory materials disposed therein, according to an embodiment.
Figure 2B:
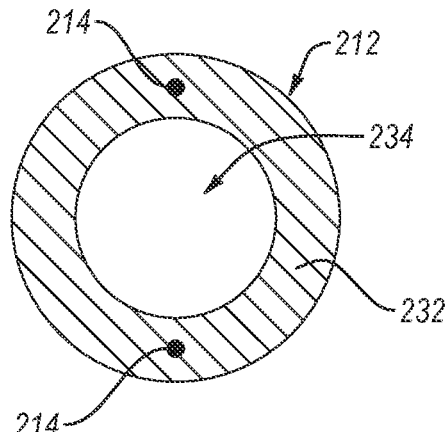
FIG. 2B is a cross-sectional schematic of the conduit taken along plane 2B-2B shown in FIG. 2A.

The fluid collection assemblies disclosed herein may include a plurality of shape memory materials disposed in the conduit. For example, FIG. 2A is a cross-sectional schematic of a conduit 212 that includes a plurality of shape memory materials 214 disposed therein, according to an embodiment. FIG. 2B is a cross-sectional schematic of the conduit 212 taken along plane 2B-2B shown in FIG. 2A. Except as otherwise disclosed herein, the conduit 212 and the shape memory materials 214 are the same or substantially similar to any of the conduits and shape memory materials disclosed herein, respectively. For example, the conduit 212 may include one or more walls 232 that define a passageway 234. Further, the conduit 212 and the shape memory materials 214 may be used in any of the fluid collection assemblies disclosed herein.

The fluid collection assembly 200 includes a plurality of shape memory materials 214 at least partially disposed in the conduit 212. For example, as illustrated, the fluid collection assembly 200 may include two shape memory materials 214 that are at least partially disposed in the conduit 212. However, it is noted that the fluid collection assembly 200 may include three or more shape memory materials 214 disposed therein, as illustrated in FIG. 3.

The plurality of shape memory materials 214, collectively, are able to maintain the shape thereof comparable to a single shape memory material 214 that exhibits a thickness that is greater than any of the plurality of shape memory materials 214. For example, the walls 232 of the conduit 212 may exhibit a thickness and each of the plurality of shape memory materials 214 may exhibit a thickness that is less than the thickness of the walls 232. However, the thickness of each of the shape memory materials 214, individually, may be unable to maintain a shape thereof during normal use of the fluid collection assembly. However, collectively, the plurality of shape memory materials 214 may be able to effectively maintain the shape thereof during normal use of the fluid collection assembly.

The shape memory materials discussed above are illustrated as extending generally parallel to a longitudinal axis of the conduit. Allowing the shape memory materials to extend generally parallel to the longitudinal axis of the conduit may facilitate formation of the conduit with the shape memory material at least partially disposed therein using a co-extrusion technique. It also minimizes a length of the shape memory material. However, shape memory materials that extend only generally parallel to the longitudinal axis may be limited in the shape that they may cause the conduit to exhibit and may be more prone to becoming dislodged from the conduit than shape memory materials that do not extend only generally parallel to the longitudinal axis. FIGS. 3-4B illustrate embodiments of shape memory materials that do not extend generally parallel to the longitudinal axis of the conduit.

Figures 3, 4A, 4B:
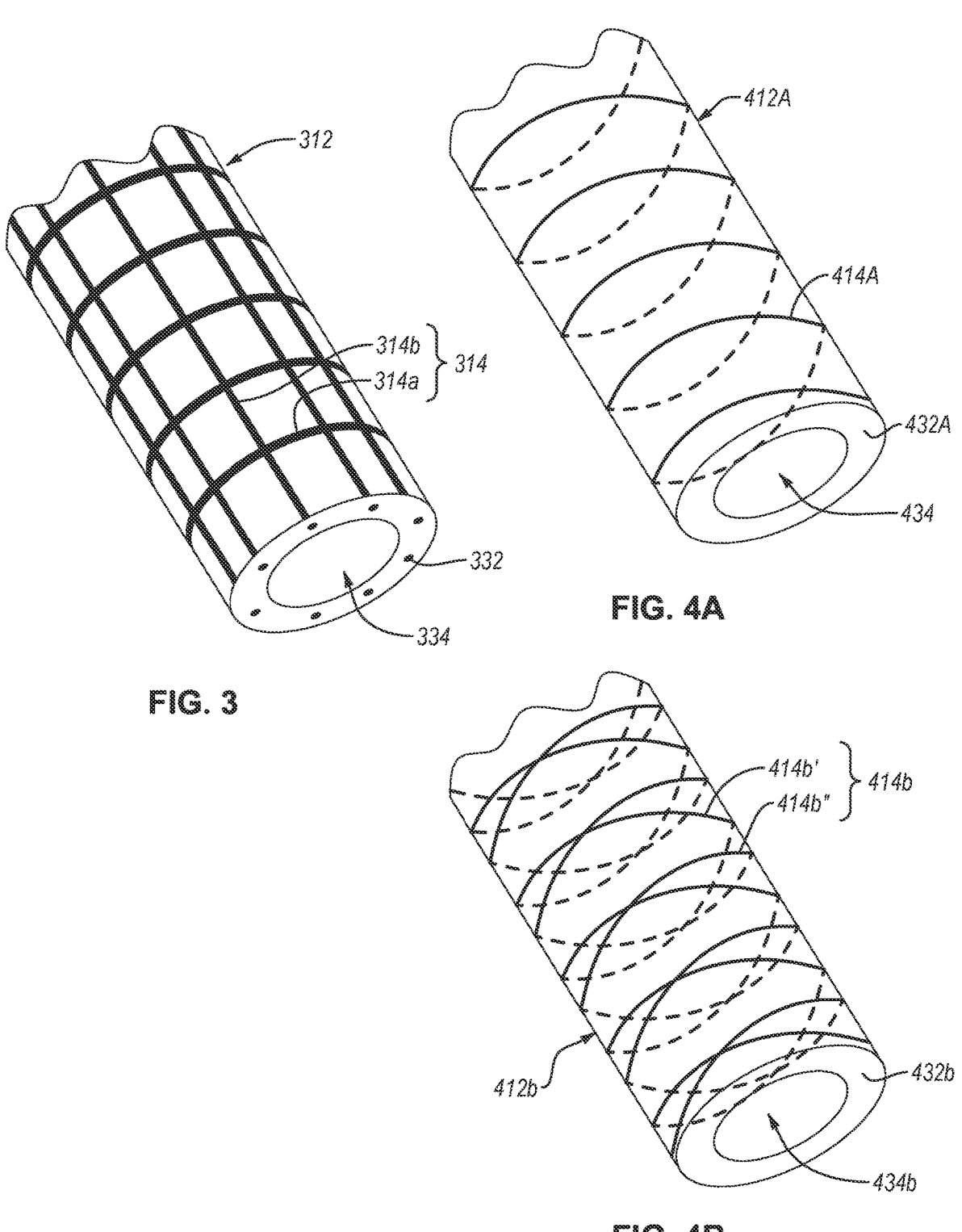
FIG. 3 is an isometric view of a portion of a conduit that includes at least one shape memory material that does not extend generally parallel to a longitudinal axis of the conduit, according to an embodiment.
FIG. 4A is an isometric view of a portion of a conduit that includes at least one shape memory material, according to an embodiment.
FIG. 4B is an isometric view of a portion of a conduit that includes a plurality of shape memory materials at least partially disposed therein, according to an embodiment.

FIG. 3 is an isometric view of a portion of a conduit 312 that includes at least one shape memory material 314 that does not extend generally parallel to a longitudinal axis of the conduit 312, according to an embodiment. Except as otherwise disclosed herein, the conduit 312 and the shape memory material 314 may be the same or substantially similarly to any of the conduits and shape memory materials disclosed herein, respectively. For example, the conduit 312 may include one or more walls 332 defining a passageway 334. For illustrative purposes, only the portion of the conduit 312 facing up is illustrated as being partially transparent while the portion of the conduit 312 facing down is illustrated as being opaque. It is noted that the conduit 312 may be at least one of transparent, translucent, or opaque. The conduit 312 and the shape memory material 314 may be used in any of the fluid collection assemblies disclosed herein.

The conduit 312 includes a plurality of shape memory materials 314. In an embodiment, as illustrated, the plurality of shape memory materials 314 include at least one first shape memory material 314a (e.g., a plurality of first shape memory materials 314a) and at least one second shape memory material 314b (e.g., a plurality of second shape memory materials 314b). The first shape memory material 314a extends generally parallel to the longitudinal axis of the conduit 312. The second shape memory material 314b does not extend generally parallel to the longitudinal axis of the conduit 312. For example, the second shape memory material 314b may extend perpendicular to the longitudinal axis of the conduit 312, such as extend circumferentially about the conduit 312 when the conduit 312 exhibits a generally cylindrical shape. In an embodiment, the shape memory material 314 may include at least one third shape memory material (not shown) that extends in a direction that is different than the first and second shape memory material 314a, 314b (e.g., the third shape memory material extends helically, as shown in FIGS. 4A and 4B). In an embodiment, the shape memory material 314 may only include one of the first shape memory material 314a or second shape memory material 314a.

In an embodiment, when the at least one first shape memory material 314a includes a plurality of first shape memory materials 314a, the second shape memory material 314b may intersect with the plurality of first shape memory materials 314a to form a wire mesh. In other words, the first and second shape memory materials 314a, 314b may be interconnected. In an embodiment, the second shape memory material 314b may be attached to (e.g., via welding, adhesive, etc.) to at least some of the first shape memory materials 314a that the second shape memory material 314b intersects. The interconnection between the first and second shape memory materials 314a, 314b may allow the shape memory material 314, as a whole, to exhibit more shapes and/or maintain the shape thereof better than if the shape memory material 314 only included one of the first or second shape memory material 314a, 314b. Further, the interconnection between the first and second shape memory materials 314a, 314b inhibits the first and second shape memory materials 314a, 314b from being dislodged from the conduit 312 since dislodging one would require dislodging the other or breaking the interconnection therebetween.

The conduit 312 may be formed using any suitable technique. In an embodiment, the first and second shape memory materials 314a, 314b may be attached to each other to maintain the positioned thereof relative to each other. After attaching the first and second shape memory materials 314a, 314b together, the first and second shape memory materials 314a, 314b may be co-extruded with the material that forms the conduit 312. It is noted that the second shape memory materials 314b may not extend completely around a circumference of the conduit 312 to allow extruder to support a portion of the die that forms the passageway 334. In an embodiment, the first and second shape memory materials 314a, 314b may be positioned relative to each other according to their desired final configuration. The first and second shape memory materials 314a, 314b may then be disposed in a mold and the material that forms the conduit 312 may be injected into the mold.

The shape memory materials may extend within the conduit in one or more directions that are not parallel and/or perpendicular to a longitudinal axis of the conduit. For example, FIG. 4A is an isometric view of a portion of a conduit 412a that includes at least one shape memory material 414a, according to an embodiment. Except as otherwise disclosed herein, the conduit 412a and the shape memory material 414a may be the same or substantially similarly to any of the conduits and shape memory materials disclosed herein, respectively. For example, the conduit 412a may include one or more walls 432a defining a passageway 434a. The conduit 412a is illustrated as being transparent for illustrative purposes, though it is noted that the conduit 412a may be opaque. Also, for illustrative purposes, the portions of the shape memory material 414a disposed in the portions of the conduit 412a facing down are illustrated using dashed lines. The conduit 412a and the shape memory material 414a may be used in any of the fluid collection assemblies disclosed herein.

The shape memory material 414a extends generally helically relative to the longitudinal axis of the conduit 412a. Such a shape memory material 414a may be more difficult to be dislodged from the conduit 412a than if the shape memory material 414a extended generally parallel to the longitudinal axis of the conduit 412a. Further, the shape memory material 414a may be formed into more shapes, such as more complex shapes, then if the shape memory material 414a extended generally parallel to the longitudinal axis of the conduit 412a.

The shape memory material 414a may be disposed in the conduit 412a using any suitable technique. In an embodiment, the shape memory material 414a may be disposed in the conduit 412a using a co-extruding technique. In such an embodiment, the shape memory material 414a may be feed through a die of the extruder in a direction that is non-parallel to the flow of the material that forms the conduit 412a. Feeding the shape memory material 414a into the die in such an non-parallel direction may cause the shape memory material 414a to exhibit the helical shape. In an embodiment, the shape memory material 414a may be forced into a helical shape, positioned in a die, and the material that forms the conduit 412*a* may be injected into the mold.

FIG. 4B is an isometric view of a portion of a conduit 412*b* that includes a plurality of shape memory materials 414*b* at least partially disposed therein, according to an embodiment. Except as otherwise disclosed herein, the conduit 412*b* and the shape memory materials 414*b* may be the same or substantially similarly to any of the conduits and shape memory materials disclosed herein, respectively. For example, the conduit 412*b* may include one or more walls 432*b* defining a passageway 434*b*. The conduit 412*b* is illustrated as being transparent for illustrative purposes, though it is noted that the conduit 412*b* may be opaque. Also, for illustrative purposes, the portions of the shape memory material 414*b* disposed in the portions of the conduit 412*b* facing down are illustrated using dashed lines. The conduit 412*b* and the shape memory materials 414*b* may be used in any of the fluid collection assemblies disclosed herein.

The plurality of shape memory materials 414*b* includes at least a first shape memory material 414*b*' and a second shape memory material 414*b*". At least one of the first or second shape memory material 414*b*', 414*b*" is at least partially disposed in the conduit 412*b*. The first shape memory material 414*b*' and the second shape memory material 414*b*" extend generally helically along the longitudinal axis of the conduit 412*b*. In an embodiment, as shown, the first shape memory 414*b*' and the second shape memory material 414*b*" exhibit different chiralities. For example, one of the first shape memory material 414*b*' or the second shape memory material 414*b*" forms a left-handed helix and the other of the first shape memory material 414*b*' or the second shape memory material 414*b*" forms a right-handed helix. The different chiralities of the first and second shape memory materials 414*b*', 414*b*" cause the first and second shape memory materials 414*b*', 414*b*" to intersect which may inhibit dislodgement of the first and second shape memory materials 414*b*', 414*b*" from the conduit 412*b*. The first and second shape memory materials 414*b*', 414*b*" having different chiralities may be formed via a co-extrusion process, for example, by feeding two different sources into the die of the extruder at different angles relative to the flow path of the material that forms the conduit 412*b*. It is noted that the first and second shape memory materials 414*b*', 414*b*" having different chiralities may be formed via other techniques, such as an injection molding technique. In an embodiment, the first shape memory 414*b*' and the second shape memory material 414*b*" exhibit the same chirality.

It is noted that, when the shape memory material includes a plurality of shape memory materials, the plurality of shape memory materials may include any combination of shape memory materials disclosed herein. For example, the plurality of shape memory materials may include at least two of at least one shape memory material that extends generally parallel to the longitudinal axis of the conduit, at least one shape memory material that extends circumferentially, or at least one shape memory material that extends helically.

Figures 5, 6A, 6B:
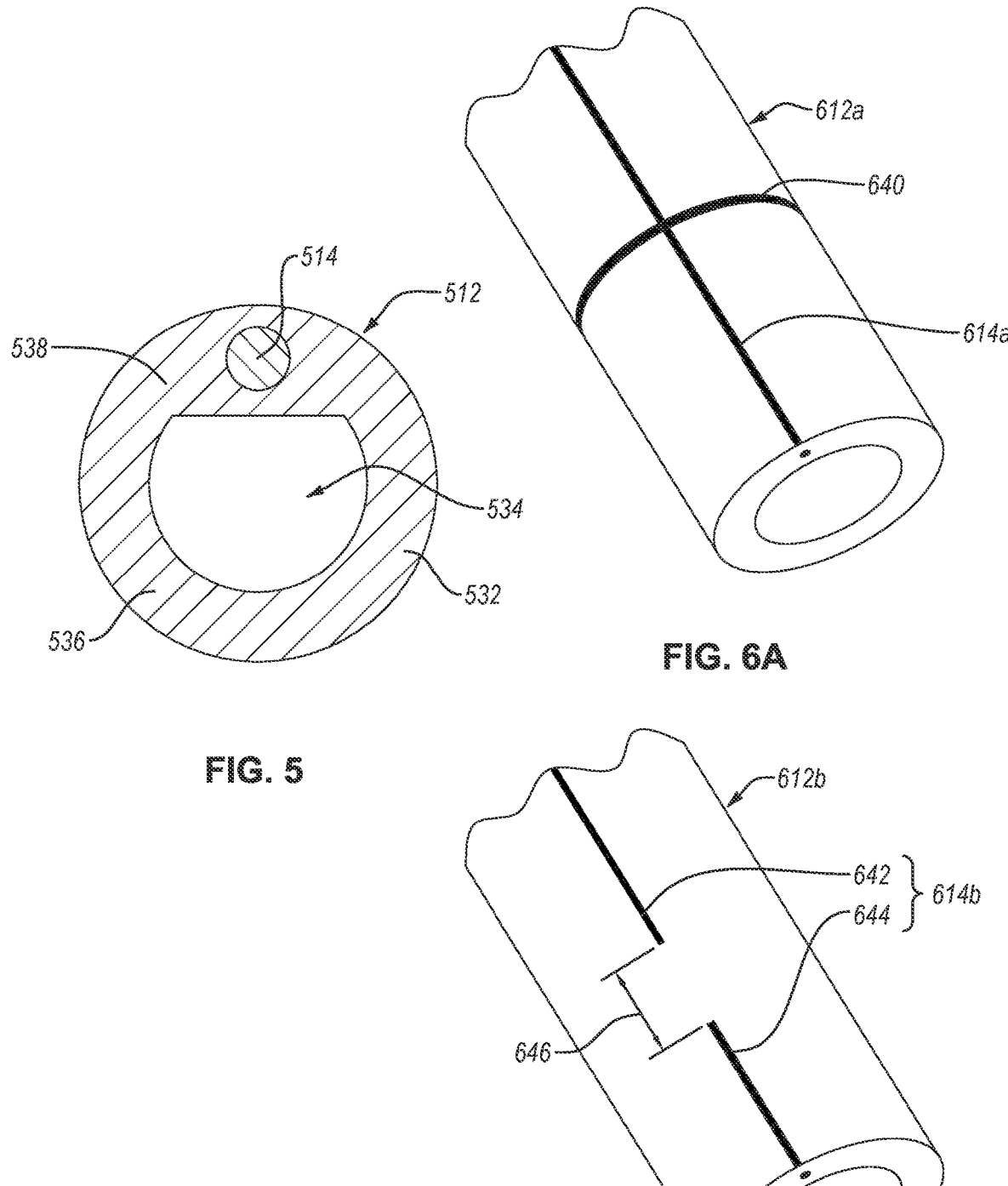
FIG. 5 is a cross-sectional schematic of a portion of a conduit that includes at least one shape memory material disposed therein, according to an embodiment.
FIG. 6A is an isometric view of a portion of a conduit that includes at least one shape memory material at least partially disposed therein, according to an embodiment.
FIG. 6B is an isometric view of a portion of a conduit that includes at least one shape memory material at least partially disposed therein, according to an embodiment.

FIG. 5 is a cross-sectional schematic of a portion of a conduit 512 that includes at least one shape memory material 514 disposed therein, according to an embodiment. Except as otherwise disclosed herein, the conduit 512 and the shape memory material 514 is the same or substantially similar to any of the conduits and shape memory materials, respectively, disclosed herein. The conduit 512 and the shape memory material 514 may be used in any of the fluid collection assemblies disclosed herein.

The conduit 512 includes one or more walls 532 and the thickness of the walls 532 may vary. For example, the one or more walls 532 may include a first portion 536 and a second portion 538. The second portion 538 may exhibit a thickness that is greater than the first portion 536. The greater thickness of the second portion 538 allows the second portion 538 to receive a shape memory material 514, for example, exhibiting at least one of a thickness that is greater than the thickness of the first portion 536 (e.g., allowing the shape memory material 514 to be completely disposed in the second portion 538) or a thickness that is sufficient great that it is difficult to maintain the shape memory material 514 attached to the first portion 536 during normal use of the fluid collection assembly.

For example, the first portion 536 of the walls 532 may exhibit a thickness that is similar to the walls of conduits that are commonly used in fluid collection assemblies (e.g., a thickness of about 1 mm to about 2 mm). The shape memory material 514 may exhibit a thickness that is sufficiently great that at least partially disposing the shape memory material 514 in the first portion 536 is not practical. One solution is to increase the thickness of the entirety of the conduit 512. However, increasing the thickness of the entirety of the conduit 512 may at least one of make the conduit 512 sufficient rigid that the shape memory material 514 struggles to change a shape thereof, decreases the volume of the chamber that may store the bodily fluids, or decrease the diameter of the passageway 534 which may decrease the rate at which the bodily fluids may be removed from the chamber. However, increasing the thickness of only a portion of the conduit 512 allows the shape memory material 514 to be securely attached to the conduit 512 (e.g., completely disposed within the walls 532) while minimizing the adverse effects of increasing the thickness of the entirety of the walls 532.

Figure 6C:
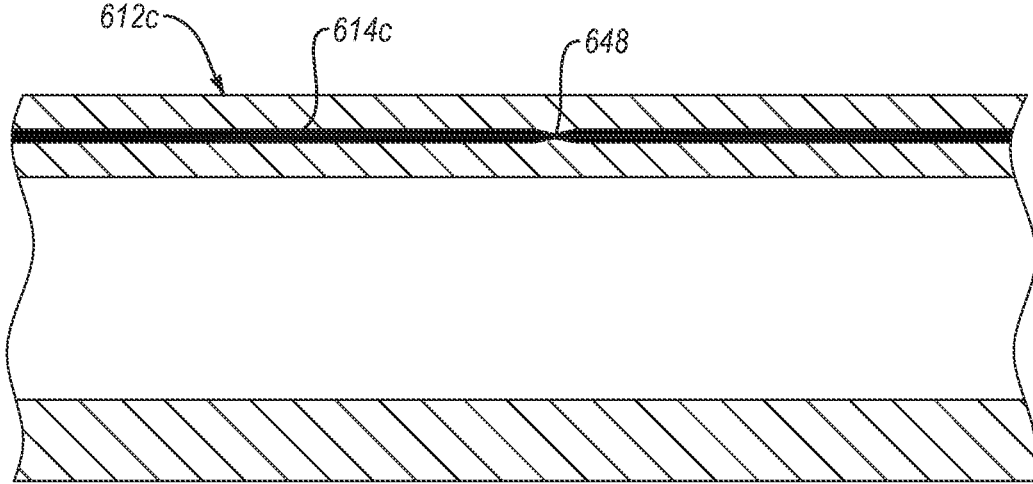
FIG. 6C is an cross-sectional schematic of a portion of a conduit that includes at least one shape memory material at least partially disposed therein, according to an embodiment.

In some embodiments, a fluid collection assembly may include a conduit, with the at least one shape memory material at least partially disposed therein, exhibiting a length that is about 12.5 cm or greater, about 15 cm or greater, about 17.5 cm or greater, about 20 cm or greater, about 22.5 cm or greater, about 25 cm or greater, about 30 cm or greater, about 40 cm or greater, about 50 cm or greater, about 75 cm or greater, about 1 m or greater, about 2 m or greater, or in ranges of about 12.5 cm to about 9.5 cm, about 15 cm to about 20 cm, about 17.5 cm to about 22.5 cm, about 20 cm to about 25 cm, about 22.5 cm to about 30 cm, about 25 cm to about 40 cm, about 30 cm to about 50 cm, about 40 cm to about 75 cm, 50 cm to about 1 m, or about 75 cm to about 2 m. It is noted that the conduit may extend from the fluid impermeable barrier and, as such, the conduit may exhibit a length that is greater than the fluid impermeable barrier. However, the conduit with the at least one shape memory material at least partially disposed therein (as formed and/or provided) may exhibit a length that is greater than the length of the conduit that is used in the fluid collection assembly. For example, the conduit with the at least one shape memory material at least partially disposed therein may be formed or provided while exhibiting a length that is about 1 m or greater, about 5 m or greater, about 10 m or greater, about 50 m or greater, or about 100 m or greater. As such, the as-formed and/or as-provided conduit may need to be cut into a plurality of conduits, wherein at least one of the plurality of conduits formed from cutting the as-formed and/or as-provided conduit is used in a fluid collection assembly. FIGS. 6A-6C illustrate different features of the as-formed and/or as-provided conduit that may facilitate cutting the as-formed and/or as-provided conduit.

FIG. 6A is an isometric view of a portion of a conduit 612a that includes at least one shape memory material 614a at least partially disposed therein, according to an embodiment. The conduit 612a is illustrated as being partially transparent for illustrative purposes, but may be at least partially opaque. Except as otherwise disclosed herein, the conduit 612a and the shape memory material 614a may be the same or substantially similar to any of the conduits and shape memory materials disclosed herein. A portion of the illustrated conduit 612a and the shape memory material 614a may be used in any of the fluid collection assemblies disclosed herein after cutting the conduit 612a and the shape memory material 614a.

The conduit 612a, as-formed and/or as-provided, exhibits a length that is greater than what is required to be disposed in a fluid collection assembly (not shown). As such, the conduit 612a may need to be cut. To facilitate cutting of the conduit 612a, the conduit 612a may include at least one marking 640 formed thereon. The marking 640 indicates a location on the conduit 612a that is to be cut. In an example, the marking 640 may indicate a location on the conduit 612a to be cut such that separated portion of the conduit 612a exhibits a desired length to be used with a fluid collection assembly. In an example, the marking 640 may indicate a location of the conduit 612a having one or more feature that facilitate cutting of the conduit 612a, such as a gap between adjacent shape memory materials 614a (as shown in FIG. 6B) or a crimped portion of the shape memory material 614 (as shown in FIG. 6C).

In an example, the marking 640 may be formed by painting or printing on a portion of the conduit 612a. In an example, the marking 640 may be a recess (e.g., divot) or protrusion that is formed on the conduit 612a. Regardless of the method used for form the marking 640, the marking 640 may be formed at some point after forming the conduit 612a, such as soon after extruding the conduit 612a from a die. It is noted that at least a portion of the marking 640 may remain on the conduit 612a after cutting the conduit 612a. For example, the conduit 612a may include at least one paint or printing thereon, may include a thinned region when the marking 640 is a recess, or a thickened region when the marking 640 is a protrusion.

As previously discussed, the shape memory materials at least partially disposed in the conduit may be formed from a metal or other hard materials. Such a shape memory material may make cutting the conduit with the shape memory material disposed therein difficult. For example, cutting the shape memory material may require the use of advanced cutting tools and/or may require more regularly replacement of the cutting tool (e.g., due to dulling of the cutting tool). As such, the shape memory materials disclosed herein may include one or more features that allows facilitates cutting the shape memory material. FIGS. 6B and 6C illustrate examples of features of the shape memory materials that may facilitate cutting thereof.

FIG. 6B is an isometric view of a portion of a conduit 612b that includes at least one shape memory material 614b at least partially disposed therein, according to an embodiment. The conduit 612b is illustrated as being transparent for illustrative purposes but may be at least partially opaque. Except as otherwise disclosed herein, the conduit 612b and the shape memory material 614b may be the same or substantially similar to any of the conduits and shape memory materials disclosed herein, respectively. The conduit 612b and the shape memory material 614b, after cutting, may be used in any of the fluid collection assemblies disclosed herein.

The shape memory material 614b is formed from a plurality of segments. For example, as illustrated, the shape memory material 614b may be formed from at least a first segment 642 and a second segment 644. The first segment 642 and the second segment 644 are distinct from each other. The first segment 642 may be spaced from the second segment 644 along the longitudinal axis of the conduit 612b by a gap 646. The gap 646 may provide a location to cut the conduit 612b without having to also cut the shape memory material 614b since the shape memory material 614b may be difficult to cut and/or may damage (e.g., dull) the tool used to cut the conduit 612b. The first segment 642 may exhibit a length that is the same or slightly smaller than the desired length of the conduit 612b that is disposed in a fluid collection assembly. The location of the gap 646 may be indicated by a marking (not shown), as previously discussed.

In an embodiment, the shape memory material 614b is disposed in the conduit 612b using a co-extrusion technique. For example, the first and second segments 642, 644 may be attached together with a material (e.g., the same material that forms the conduit 612b) that is easier to cut than the first and second segments 642, 644. Connecting the first and second segments 642, 644 together with the material allows the first and second segments 642, 644 to be spooled into the die. It is noted that the first and second segments 642, 644 do not need to be connected together to be co-extruded. In an embodiment, the shape memory material 614b is at least partially disposed in the conduit 612b by positioning the shape memory material 614b (e.g., the first and second segments 642, 644) in a mold and the material that forms the conduit 612b is injected into the mold.

FIG. 6C is an cross-sectional schematic of a portion of a conduit 612c that includes at least one shape memory material 614c at least partially disposed therein, according to an embodiment. The conduit 612c is illustrated as being transparent for illustrative purposes but may be at least partially opaque. Except as otherwise disclosed herein, the conduit 612c and the shape memory material 614c may be the same or substantially similar to any of the conduits and shape memory materials disclosed herein, respectively. The conduit 612c and the shape memory material 614c, after cutting, may be used in any of the fluid collection assemblies disclosed herein.

The shape memory material 614c exhibits a thickness measured traverse to a longitudinal axis of the conduit 612c (e.g. measured radially). The thickness of the shape memory material 614c may be selectively varied. The variation of the thickness of the shape memory material 614c may vary to facilitate cutting of the shape memory material 614c. For example, the shape memory material 614c may include at least one narrowed region 648 that exhibits a thickness that is less than the portions of the shape memory material 614c thereabout. The narrowed region 648 may facilitate cutting the shape memory material 614c since the cutting tool only needs to cut through a smaller thickness of the shape memory material 614c. For instance, the narrowed region 648 may exhibit a smaller cross-sectional area than the portions of the shape memory material 614c thereabout or may engage a greater surface area of the cutting tool while being cut thereby better distributing wear across the cutting tool.

The narrowed region 648 may be formed by crimping the shape memory material 614c, grinding, otherwise mechanically removing portions of the shape memory material 614c, or otherwise thinning at least one portion of the shape memory material 614c. The narrowed region 648 may be formed before at least partially disposing the shape memory material 614c in the conduit 612c.

Changing the shape of the shape memory materials disclosed herein, for example, from the first shape to the second shape, causes the conduit to change a shape thereof. In some embodiments, changing the shape of the conduit presses against the porous material to change the shape of the porous material. Further, changing the shape of the porous material also causes the porous material to press against the fluid impermeable barrier to change the shape of the fluid impermeable barrier. Generally, the porous material and the fluid impermeable barrier resist a change in the shape thereof less than the conduit. However, the porous material and the fluid impermeable barrier do resist changes in the shape thereof which causes a compressive force to be applied to the porous material. The compressive force applied to the porous material may decrease the quantity of bodily fluids that may be stored in the porous material which increases the likelihood that the porous material becomes saturated with bodily fluids and leaks.

Figures 7A, 7B:
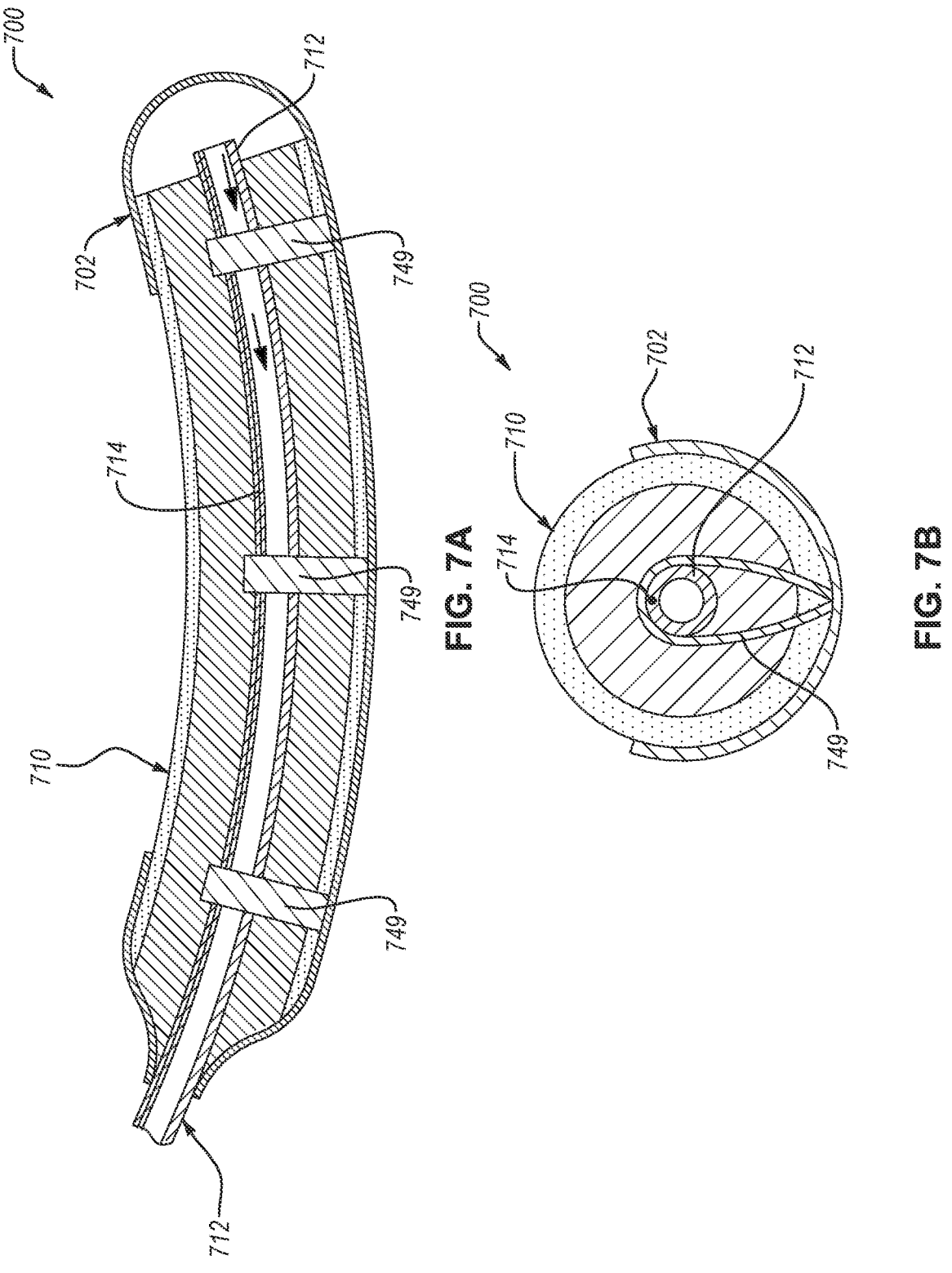
FIG. 7A is a cross-sectional schematic of a fluid collection assembly, according to an embodiment.
FIG. 7B is a cross-sectional schematic of the fluid collection assembly taken along plane 7B-7B of FIG. 7A.

The fluid collection assemblies disclosed herein may include one or more structure that are configured to limit the compressive force applied to the porous material. In particular, the structures may be configured to transfer the change of shape of the conduit to the fluid impermeable barrier substantially without using the porous material as an intermediary. FIG. 7A is a cross-sectional schematic of a fluid collection assembly 700, according to an embodiment. FIG. 7B is a cross-sectional schematic of the fluid collection assembly 700 taken along plane 7B-7B of FIG. 7A. Except as otherwise disclosed herein, the fluid collection assembly 700 is the same or substantially similar to any of the fluid collection assemblies disclosed herein. For example, the fluid collection assembly 700 includes a fluid impermeable barrier 702, a porous material 710, a conduit 712, and a shape memory material 714 at least partially disposed in the conduit 712.

The fluid collection assembly 700 includes at least one brace 749 that is configured to force the fluid impermeable barrier 702 to exhibit a shape change that corresponds more closely to the shape change of the shape memory material 714 (e.g., the shape change of the conduit 712) than if the fluid collection assembly 700 did not include the brace 749. The brace 749 also minimizes the compressive force applied to the porous material 710. The brace 749 is connected to (e.g., extends around) the conduit 712 The brace 749 extends from the conduit 712 to the fluid impermeable barrier 702. The brace 749 is attached to the fluid impermeable barrier 702, such as with an adhesive. To allow the brace 749 to extend from the conduit 712 to the fluid impermeable barrier 702, one or more components of the fluid collection assembly 700 (e.g., the porous material 710) may include one or more slits formed therein through which the brace 749 extend. The brace 749 may be configured to transfer a shape change in the shape memory material 714 to the fluid impermeable barrier 702 such that the fluid impermeable barrier 702 exhibits a shape change that substantially corresponds to the shape change of the shape memory material 714.

The fluid collection assembly 700 may include any suitable number of braces 749, such as 1, 2, 3, 4, 5, 6, 7, 8, 7, 10, or greater than 10 braces 749. Generally increasing the number of braces 749 causes the fluid impermeable barrier 702 to more accurately correspond to the shape of the shape memory material 714 and decreases the normal force that is applied to the porous material 710.

It is noted that the braces 749 may not always cause the fluid impermeable barrier 702 to exhibit the same shape change as the shape memory material 714. For example, when the braces 749 are looped around and are not attached to the conduit 712 (as shown), the braces 749 may only cause the fluid impermeable barrier 702 to exhibit the shape change of the shape memory material 714 when the braces 749 pull (e.g., the braces 749 are in tension) the fluid impermeable barrier 702 towards the conduit 712 but not when the braces 749 push (e.g., the braces 749 are in compression) the fluid impermeable barrier 702 away from the conduit 712.

In an embodiment, the braces 749 are formed from any of the shape memory materials disclosed herein. In an embodiment, the braces 749 may be formed from a non-shape memory material, such as fabric.

FIG. 8 is a block diagram of a system 850 for fluid collection, according to an embodiment. The system 850 includes a fluid collection assembly 800, a fluid storage container 852, and a vacuum source 854. The fluid collection assembly 800, the fluid storage container 852, and the vacuum source 854 may be fluidly coupled to each other via one or more conduits 856. At least a portion of the conduit 856 may include at least one shape memory material at least partially disposed therein, such as a portion of the conduit 856 that is disposed in and forms part of. the fluid collection assembly 800. In some embodiments, a portion of the conduit 856 (e.g., the portions of the conduit 856 spaced from the fluid collection assembly 800) do not include at least one shape memory material disposed therein.

The fluid collection assembly 800 may be operably coupled to one or more of the fluid storage container 852 or the vacuum source 854 via the conduit 856. Fluid (e.g., urine or other bodily fluids) collected in the fluid collection assembly 800 may be removed from the fluid collection assembly 800 via the conduit 856 which protrudes into the fluid collection assembly 800. For example, an inlet of the conduit 856 may extend into the fluid collection assembly 800, such as to a fluid reservoir thereof. The outlet of the conduit 856 may extend into the fluid collection assembly 800 or the vacuum source 854. Suction force may be introduced into the chamber of the fluid collection assembly 800 via the inlet of the conduit 856 responsive to suction (e.g., vacuum) force applied at the outlet of the conduit 856.

The suction force may be applied to the outlet of the conduit 856 by the vacuum source 854 either directly or indirectly. The suction force may be applied indirectly via the fluid storage container 852. For example, the outlet of the conduit 856 may be disposed within the fluid storage container 852 and an additional conduit 856 may extend from the fluid storage container 852 to the vacuum source 854. Accordingly, the vacuum source 854 may apply suction to the fluid collection assembly 800 via the fluid storage container 852. The suction force may be applied directly via the vacuum source 854. For example, the outlet of the conduit 856 may be disposed within the vacuum source 854. An additional conduit 856 may extend from the vacuum source 854 to a point outside of the fluid collection assembly 800, such as to the fluid storage container 852. In such examples, the vacuum source 854 may be disposed between the fluid collection assembly 800 and the fluid storage container 852.

The fluid collection assembly 800 may be similar or identical to any of the fluid collection assemblies disclosed herein in one or more aspects. The fluid collection assembly 800 may be shaped and sized to be positioned adjacent to a female urethral opening. For example, the fluid collection assembly 800 may include a fluid impermeable barrier at least partially defining a chamber (e.g., interior region) of the fluid collection assembly 800. The fluid impermeable barrier also defines an opening extending therethrough from the external environment. The opening may be positioned adjacent to a female urethral opening. The fluid collection assembly 800 may include may include at least one porous material disposed in the chamber such as one or more of a fluid permeable support and a fluid permeable membrane. The fluid collection assembly 800 includes the shape memory material at least partially disposed in a conduit (e.g., conduit 856) that is at least partially disposed in the chamber. The shape memory material is sized, shaped, and positioned to retain a selected geometric configuration as disclosed herein. The conduit 856 may extend into the fluid collection assembly 800, through one or more of the fluid impermeable barrier, fluid permeable membrane, or the fluid permeable support to a distal end region of the fluid collection assembly 800. The conduit 856 includes an inlet and an outlet, the outlet being fluidly coupled to the fluid storage container 852 and the inlet being positioned in a portion of the chamber selected to be at a gravimetrically low point of the fluid collection assembly 800 when worn.

The fluid storage container 852 is sized and shaped to retain a fluid therein. The fluid storage container 852 may include a bag (e.g., drainage bag), a bottle or cup (e.g., collection jar), or any other enclosed container for storing the bodily fluids, such as urine. In some examples, the conduit 856 may extend from the fluid collection assembly 800 and attach to the fluid storage container 852 at a first point therein. An additional conduit 856 may attach to the fluid storage container 852 at a second point thereon and may extend and attach to the vacuum source 854. Accordingly, a vacuum (e.g., suction) may be drawn through fluid collection assembly 800 via the fluid storage container 852. The bodily fluids may be drained from the fluid collection assembly 800 using the vacuum source 854.

The vacuum source 854 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 854 may provide a vacuum or suction to remove fluid from the fluid collection assembly 800. In some examples, the vacuum source 854 may be powered by one or more of a power cord (e.g., connected to a power socket), one or more batteries, or even manual power (e.g., a hand operated vacuum pump). In some examples, the vacuum source 854 may be sized and shaped to fit outside of, on, or within the fluid collection assembly 800. For example, the vacuum source 854 may include one or more miniaturized pumps or one or more micro pumps. The vacuum sources 854 disclosed herein may include one or more of a switch, a button, a plug, a remote, or any other assembly suitable to activate the vacuum source 854.

Figure 9:
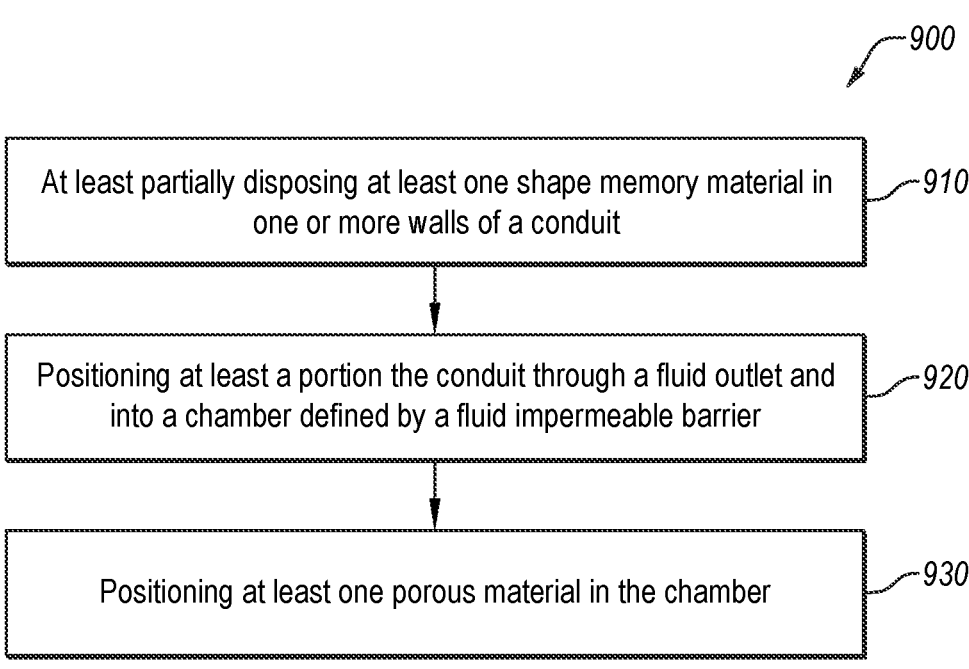
FIG. 9 is flow diagram of a method to form any of the fluid collection assemblies disclosed herein.

FIG. 9 is flow diagram of a method 900 to form any of the fluid collection assemblies disclosed herein. The method 900 may include act 910, which recites "at least partially disposing at least one shape memory material in one or more walls of a conduit." Act 910 may be followed by act 920, which recites "positioning at least a portion the conduit through a fluid outlet and into a chamber defined by a fluid impermeable barrier." Act 920 may be followed by act 930, which recites "positioning at least one porous material in the chamber."

Acts 910, 920, 930 of the method 900 are for illustrative purposes. For example, the act 910, 920, 930 of the method

900 may be performed in different orders, split into multiple acts, modified, supplemented, or combined. In an example, one or more of the acts 910, 920, 930 of the method 900 may be omitted from the method 900.

Act 910 recites "at least partially disposing at least one shape memory material in one or more walls of a conduit." The shape memory material may be disposed in the one or more walls of the conduit using any of the techniques disclosed herein or any other suitable technique. In an example, the shape memory material may be disposed in the one or more walls of the conduit using a co-extrusion technique that includes co-extruding at least one polymer that forms the conduit and the at least one shape memory material. The co-extrusion technique may include feeding the shape memory material into a die in a direction that is substantially parallel to the flow of the polymer if the shape memory material extends parallel to the longitudinal axis of the conduit. The co-extrusion technique may include feeding the shape memory material into a die in a direction that is not parallel to the flow of the polymer if the shape memory material does not extend parallel to the longitudinal axis of the conduit (e.g., the shape memory material is helical). In an example, the shape memory material may be disposed in the conduit using an injection molding technique. The injection molding technique may include positioning the shape memory material in a mold and injecting the one or more polymers that form the conduit into the mold.

In an embodiment, act 910 includes forming a conduit that needs to be cut because the conduit, as formed and/or as provided, exhibits a length that is too long for a single fluid collection assembly. In such an embodiment, the method 900 may include cutting the conduit into two or more pieces wherein only one of the pieces is configured to be positioned through the fluid outlet and into the chamber of each fluid collection assembly. Cutting the conduit may include cutting one or more markings formed on the conduit, cutting the conduit at a gap between two segments of the shape memory material, or cutting the shape memory material at a narrowed region thereof.

After act 910, the method 900 includes acts 920 and 930. Act 920 recites "positioning at least a portion the conduit through a fluid outlet and into a chamber defined by a fluid impermeable barrier" and act 930 recites "positioning at least one porous material in the chamber." Acts 920 and 930 may be performed in any order or may be performed simultaneously.

Figure 10:
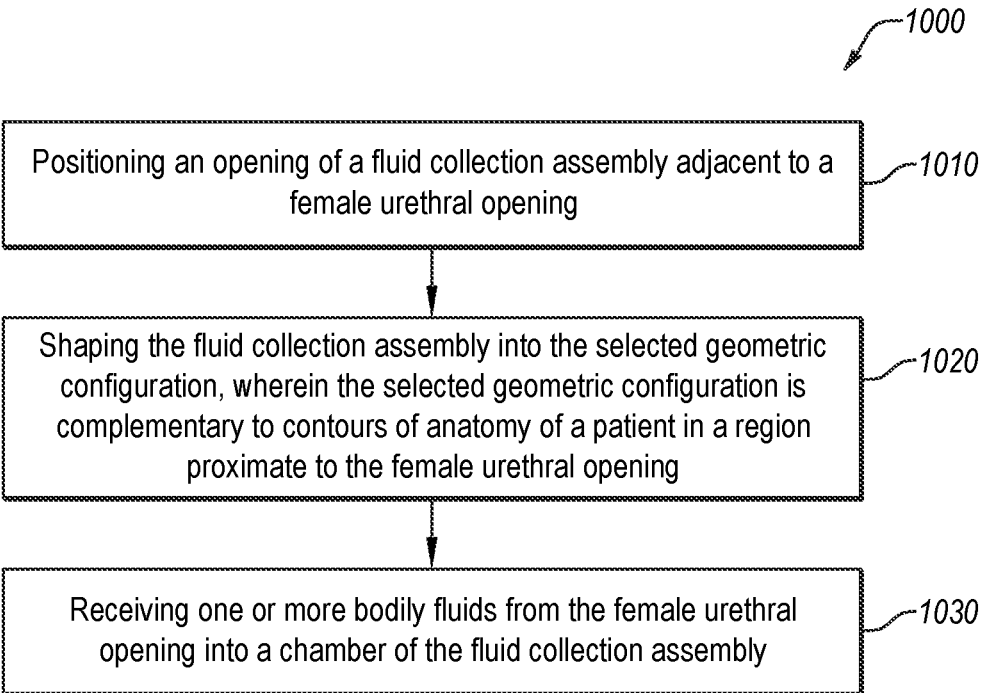
FIG. 10 is a flow diagram of a method to collect one or more bodily fluids, according to an embodiment.

FIG. 10 is a flow diagram of a method 1000 to collect one or more bodily fluids, according to an embodiment. The method 1000 of collecting bodily fluids may utilize use any of the fluid collection assemblies and/or fluid collection systems disclosed herein. The method 1000 may include act 1010, which recites "positioning an opening of a fluid collection assembly adjacent to a female urethral opening." Act 1010 may be followed by act 1020, which recites "shaping the fluid collection assembly into the selected geometric configuration, wherein the selected geometric configuration is complementary to contours of anatomy of a patient in a region proximate to the female urethral opening." Act 1020 may be followed by act 1030, which recites "receiving one or more bodily fluids from the female urethral opening into a chamber of the fluid collection assembly."

Acts 1010, 1020, 1030 of the method 1000 are for illustrative purposes. For example, the act 1010, 1020, 1030 of the method 1000 may be performed in different orders, split into multiple acts, modified, supplemented, or combined. In an example, one or more of the acts 1010, 1020,

1030 of the method 1000 may be omitted from the method 1000. Any of the acts 1010, 1020, or 1030 may include using any of the fluid collection assemblies or systems disclosed herein.

Act 1010 recites "positioning an opening of a fluid collection assembly adjacent to a female urethral opening." The act 1010 of positioning an opening of a fluid collection assembly adjacent to a female urethral opening may include utilizing any of the fluid collection assemblies or systems disclosed herein. In some examples, act 1010 may include positioning the opening of a female fluid collection assembly such that the fluid permeable membrane of the female fluid collection assembly abuts or is positioned proximate to the female urethral opening. In some examples, positioning an opening of a fluid collection assembly adjacent to a female urethral opening may include positioning the opening over the female urethral opening, such as positioning a longitudinally extending opening of the fluid collection assembly over the female urethral opening.

Act 1020 recites "shaping the fluid collection assembly into the selected geometric configuration, wherein the selected geometric configuration is complementary to contours of anatomy of a patient in a region proximate to the female urethral opening." Shaping the fluid collection assembly into the selected geometric configuration may include forming the fluid collection assembly into a second shape that is different than a first shape or vice versa. Shaping the fluid collection assembly into the selected shape may include shaping a female fluid collection assembly to contour to the anatomy around the urethral opening of a female patient. In some embodiments, shaping the fluid collection assembly into the selected geometric configuration includes forming the (e.g., a longitudinal shape of the) fluid collection assembly into an arcuate shape conforming to the perineal region of the patient. For example, shaping the fluid collection assembly into the selected geometric configuration may include forming the fluid collection assembly into an arcuate shape conforming to the vaginal and perineal region of a patient. In some embodiments, shaping the fluid collection assembly into the selected geometric configuration includes flattening or rounding a lateral cross-section of the fluid collection assembly.

Shaping the fluid collection assembly into the selected geometric configuration may include manually bending, stretching, compressing, or otherwise manipulating at least one portion of the fluid collection assembly to the selected geometric configuration. In some embodiments, shaping the fluid collection assembly into the selected geometric configuration includes flattening or rounding a lateral cross-section of the fluid collection assembly. In some embodiments, shaping the fluid collection assembly into the selected geometric configuration includes compressing or bending a the fluid collection assembly longitudinally.

Act 1030 recites, "receiving one or more bodily fluids from the female urethral opening into a chamber of the fluid collection assembly." In some examples, receiving fluid from the female urethral opening into a chamber of the fluid collection assembly includes receiving the fluid through the opening of the fluid collection assembly. Receiving fluid from the female urethral opening into a chamber of the fluid collection assembly may include wicking the bodily fluids away from the opening using porous material, such as via a fluid permeable membrane and a fluid permeable support. Receiving fluid from the female urethral opening into a chamber of the fluid collection assembly may include flowing the bodily fluids towards a portion of the chamber that is fluidly coupled to an inlet of a conduit in fluid communication a vacuum source. For instance, receiving the bodily fluid from the female urethral opening into a chamber of the fluid collection assembly may include flowing the bodily fluids to a substantially unoccupied portion of the chamber (e.g., a reservoir), to a gravimetrically low point of the chamber, etc., such as via gravity, wicking, or suction force. In some examples, wicking the fluid into the chamber via the fluid permeable membrane and fluid permeable support may include wicking urine into a reservoir in the fluid collection assembly.

The method 1000 may include applying suction with a vacuum source effective to suction the bodily fluids from the chamber via a conduit disposed therein and fluidly coupled to the vacuum source may include using any of the vacuum sources disclosed herein. Applying suction with a vacuum source may include activating the vacuum source (e.g., suction assembly) in fluid communication with the inlet of the conduit in the fluid collection assembly. In some examples, activating the vacuum source in fluid communication with the inlet of the conduit in the fluid collection assembly may include supplying power to the vacuum source by one or more of flipping an on/off switch, pressing a button, plugging the vacuum source into a power outlet, putting batteries into the vacuum source, etc. In some examples, the vacuum source may include a hand operated vacuum pump and applying suction with a vacuum source may include manually operating the hand operated vacuum pump effective to suction the bodily fluids from the chamber via the conduit disposed therein that is fluidly coupled to the vacuum source.

In some examples, applying suction with a vacuum source effective to suction the bodily fluids from the chamber via a conduit disposed therein and fluidly coupled to the vacuum source may be effective to remove at least some bodily fluids (e.g., urine) from the chamber (e.g., interior region) of the fluid collection assembly. In some examples, applying suction with a vacuum source effective to suction the bodily fluids from the chamber via a conduit disposed therein and fluidly coupled to the vacuum source may be effective to transfer at least some of the bodily fluids from the chamber to a fluid storage container (e.g., a bottle or bag), such as from one or more of a reservoir, fluid permeable support, or fluid permeable membrane.

In some examples, the vacuum source (e.g., suction assembly) may be disposed on or within the fluid collection assembly and applying suction with the vacuum source may include activating the vacuum source. In some examples, the vacuum source may be spaced from the fluid collection assembly and applying suction with the vacuum source may include activating the vacuum source.

In some examples, applying suction with a vacuum source effective to suction the bodily fluids from the chamber via a conduit disposed therein and fluidly coupled to the vacuum source may include detecting moisture in the chamber (e.g., via one or more moisture sensors) and responsive thereto, activating the vacuum source to provide suction in the chamber. The control of the vacuum source responsive to the signals indicating that moisture or a level thereof is present in the chamber may be automatic, such as via a controller (e.g., computer programmed to perform the operation), or may merely provide an indication that a level of moisture is present that may necessitate removal of the bodily fluids from the chamber of the fluid collection assembly. In the latter case, a patient may receive the indication (e.g., from the controller) and activate the vacuum pump manually.

In an example, the method 1000 may include collecting the bodily fluids that are removed from the fluid collection assembly, such as into a fluid storage container that is spaced from the fluid collection assembly and fluidly coupled to the conduit. The fluid storage container may include any of the fluid storage containers disclosed herein.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean±10%, ±5%, or +2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

We claim:

1. A fluid collection assembly, comprising:
a fluid impermeable barrier at least partially defining a chamber, at least one opening configured to be positioned adjacent to a female urethral opening, and a fluid outlet;
at least one porous material disposed in the chamber;
a conduit extending from the fluid outlet into the chamber, the conduit including one or more walls that define a passageway, the conduit including an inner surface defining the passageway and an outer surface opposite the inner surface, wherein an entirety of the outer surface of the conduit extending into the chamber is circular in a cross-sectional plane that is perpendicular to a longitudinal axis of the conduit; and
at least one shape memory material completely disposed within the one or more walls of the conduit, the at least one shape memory material includes at least a first shape memory material extending substantially parallel to the longitudinal axis of the conduit along at least substantially all of a length of the conduit in the chamber, the at least one shape memory material being sized, shaped, and positioned in the one or more walls to retain a selected geometric configuration, the first shape memory material including two terminal ends longitudinally spaced from each other and exhibiting single piece construction extending continuously between the two terminal ends, each of the two terminal ends spaced from adjacent terminal ends of the conduit; and
wherein the one or more walls of the conduit includes a first portion and a second portion, the first portion configured to receive the at least one shape memory material, the first portion exhibiting a thickness that is different than a thickness of the second portion, the thickness of the first portion and the thickness of the second portion measured from the outer surface of the one or more walls to the immediately adjacent inner surface, the thickness of the first portion and the thickness of the second portion remains substantially constant along the longitudinal axis of the conduit; and
wherein the fluid impermeable barrier and the at least one porous material define a fluid reservoir that is substantially unoccupied, and wherein the at least one shape memory material and portions of the conduit having the at least one shape memory material disposed therein do not extend into the fluid reservoir.

2. The fluid collection assembly of claim 1, wherein the at least one shape memory material includes steel, aluminum, or copper.

3. The fluid collection assembly of claim 1, wherein the at least one shape memory material includes one or more wires.

4. The fluid collection assembly of claim 3, wherein the one or more wires includes a plurality of wires.

5. The fluid collection assembly of claim 1, wherein the at least one shape memory material further includes at least one second shape memory material, wherein the first shape memory material and the at least one second shape memory material intersect.

6. The fluid collection assembly of claim 1, wherein the at least one shape memory material further includes at least one second shape memory material that extends generally helically.

7. The fluid collection assembly of claim 1, wherein the at least one shape memory material exhibits a thickness that is about 1.5 mm or less.

8. The fluid collection assembly of claim 1, wherein the at least one shape memory material exhibits a thickness that is less than a thickness of the one or more walls.

9. A system comprising:
the fluid collection assembly of claim 1;
a fluid storage container configured to hold a fluid; and
a vacuum source fluidly coupled to one or more of the fluid storage container or the fluid collection assembly via the conduit, the vacuum source configured to remove fluid from the fluid collection assembly via the conduit.

10. A method to collect one or more bodily fluids, the method comprising:
positioning an opening of a fluid collection assembly adjacent to a female urethral opening, the fluid collection assembly including:
a fluid impermeable barrier at least partially defining a chamber, at least one opening configured to be positioned adjacent to a female urethral opening, and a fluid outlet;
at least one porous material disposed in the chamber;
a conduit extending from the fluid outlet into the chamber, the conduit including one or more walls that define a passageway, the conduit including an inner surface defining the passageway and an outer surface opposite the inner surface, wherein an entirety of the outer surface of the conduit extending into the chamber is circular in a cross-sectional plane that is perpendicular to a longitudinal axis of the conduit; and
at least one shape memory material completely disposed within the one or more walls of the conduit, the at least one shape memory material includes at least a first shape memory material extending substantially parallel to the longitudinal axis of the conduit along at least substantially all of a length of the conduit in the chamber, the at least one shape memory material being sized, shaped, and positioned to retain a selected geometric configuration, the first shape memory material including two terminal ends longitudinally spaced from each other and exhibiting single piece construction extending continuously between the two terminal ends, each of the two terminal ends spaced from adjacent terminal ends of the conduit;

wherein the one or more walls of the conduit includes a first portion and a second portion, the first portion configured to receive the at least one shape memory material, the first portion exhibiting a thickness that is different than a thickness of the second portion, the thickness of the first portion and the thickness of the second portion measured from the outer surface of the one or more walls to the immediately adjacent inner surface, the thickness of the first portion and the thickness of the second portion remains substantially constant along the longitudinal axis of the conduit; and wherein the fluid impermeable barrier and the at least one porous material define a fluid reservoir that is substantially unoccupied, and wherein the at least one shape memory material and portions of the conduit having the at least one shape memory material disposed therein do not extend into the fluid reservoir;

shaping the fluid collection assembly into the selected geometric configuration, wherein the selected geometric configuration is complementary to contours of anatomy of a patient in a region proximate to the female urethral opening; and receiving the one or more bodily fluids from the female urethral opening into a chamber of the fluid collection assembly.

11. The fluid collection assembly of claim 1, wherein all of the at least one shape memory material is completely disposed in the first portion.

12. The fluid collection assembly of claim 1, wherein the one or more walls of the conduit include a uniform material.

13. The fluid collection assembly of claim 1, wherein the one or more walls of the conduit exhibit single piece construction.

14. The fluid collection assembly of claim 1, wherein all of the conduit is an extruded conduit.

15. The fluid collection assembly of claim 1, wherein the first shape memory material includes a metal; and further comprising at least one polymer shape memory material that is distinct and separate from the conduit, the at least one polymer shape memory material is deformable.

16. The fluid collection assembly of claim 1, wherein the first shape memory material is disposed in a portion of the conduit that is opposite the at least one opening.

* * * * *